United States Patent
Moses et al.

(10) Patent No.: US 12,241,888 B2
(45) Date of Patent: Mar. 4, 2025

(54) PLATFORM FOR ASSESSMENT OF THE TRANSCYTOSIS OF EXTRACELLULAR VESICLES ACROSS ENDOTHELIAL BARRIERS AND USES THEREOF

(71) Applicant: Children's Medical Center Corporation, Boston, MA (US)

(72) Inventors: Marsha A. Moses, Brookline, MA (US); Golnaz Morad, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 1150 days.

(21) Appl. No.: 16/979,710

(22) PCT Filed: Mar. 14, 2019

(86) PCT No.: PCT/US2019/022194
§ 371 (c)(1),
(2) Date: Sep. 10, 2020

(87) PCT Pub. No.: WO2019/178317
PCT Pub. Date: Sep. 19, 2019

(65) Prior Publication Data
US 2021/0041421 A1    Feb. 11, 2021

Related U.S. Application Data

(60) Provisional application No. 62/643,145, filed on Mar. 14, 2018.

(51) Int. Cl.
*G01N 33/50* (2006.01)
*A61K 31/4709* (2006.01)
*A61K 31/517* (2006.01)
*G01N 33/574* (2006.01)

(52) U.S. Cl.
CPC ..... *G01N 33/5064* (2013.01); *A61K 31/4709* (2013.01); *A61K 31/517* (2013.01); *G01N 33/57415* (2013.01); *G01N 33/57419* (2013.01); *G01N 33/57423* (2013.01); *G01N 33/5743* (2013.01); *G01N 33/57438* (2013.01)

(58) Field of Classification Search
None
See application file for complete search history.

(56) References Cited

U.S. PATENT DOCUMENTS

| | | |
|---|---|---|
| 9,921,223 B2 | 3/2018 | Kalluri et al. |
| 2010/0273200 A1 | 10/2010 | Niwa et al. |
| 2011/0053157 A1 | 3/2011 | Skog et al. |
| 2013/0224110 A1 | 8/2013 | Bynoe |
| 2014/0248268 A1 | 9/2014 | Wandinger-Ness et al. |
| 2016/0354313 A1 | 12/2016 | De Beer et al. |
| 2018/0036240 A1 | 2/2018 | Gho et al. |
| 2018/0274035 A1 | 9/2018 | Ochiya et al. |
| 2022/0249570 A1 | 8/2022 | Kim et al. |
| 2022/0275371 A1 | 9/2022 | Moses et al. |
| 2022/0288241 A1 | 9/2022 | Moses et al. |

FOREIGN PATENT DOCUMENTS

| | | |
|---|---|---|
| CN | 108175759 A | 6/2018 |
| WO | WO 2016/201323 A1 | 12/2016 |
| WO | WO 2018/145211 A1 | 8/2018 |
| WO | WO 2019/027847 A1 | 2/2019 |
| WO | WO 2019/151744 A1 | 8/2019 |
| WO | WO 2019/178317 A1 | 9/2019 |

OTHER PUBLICATIONS

Rubin et al. "A Cell Culture Model fo the Blood-Brain Barrier", (1991), J Cell Biol, vol. 115, No. 6: 1725-1735 (Year: 1991).*
Jang et al., Bioinspired exosome-mimetic nanovesicles for targeted delivery of chemotherapeutics to malignant tumors. ACS Nano. Sep. 24, 2013;7(9):7698-710. doi: 10.1021/nn402232g. Epub Sep. 4, 2013.
Silva et al., Combining magnetic nanoparticles with cell derived microvesicles for drug loading and targeting. Nanomedicine. Apr. 2015;11(3):645-55. doi: 10.1016/j.nano.2014.11.009. Epub Jan. 14, 2015.
Wu et al., Exosome-Mimetic Nanovesicles from Hepatocytes promote hepatocyte proliferation in vitro and liver regeneration in vivo. Sci Rep. Feb. 6, 2018;8(1):2471. 11 pages. doi: 10.1038/s41598-018-20505-y.
Chen et al., Elucidation of Exosome Migration across the Blood-Brain Barrier Model In Vitro. Cell Mol Bioeng. Dec. 2016;9(4):509-529.
Cui et al., Expression of MicroRNA-301a and its Functional Roles in Malignant Melanoma. Cell Physiol Biochem. 2016;40(1-2):230-244.
De Graauw et al., Annexin A1 regulates TGF-beta signaling and promotes metastasis formation of basal-like breast cancer cells. Proc Natl Acad Sci U S A. Apr. 6, 2010;107(14):6340-5.
Gonzalez-Mariscal et al., Crosstalk of tight junction components with signaling pathways Biochim Biophys Acta. Mar. 2008; 1778(3):729-56.

(Continued)

*Primary Examiner* — Teresa E Knight
(74) *Attorney, Agent, or Firm* — Wolf, Greenfield & Sacks, P.C.

(57) ABSTRACT

Provided herein are methods of determining whether an extracellular vesicle (EV) can cross an endothelial barrier (e.g., the blood brain barrier). In some embodiments, the EV originates from a cancer cell. In some embodiments, the cancer has a higher likelihood of metastasizing (to the brain) if the EV originating from a cancer cell is determined to be able to cross an endothelial barrier (e.g., the blood brain barrier). Thus, further provided herein are methods of determining whether a subject who has cancer is likely to develop metastatic cancer. In some embodiments, the subject is treated for the metastatic cancer accordingly.

21 Claims, 21 Drawing Sheets

(56) References Cited

OTHER PUBLICATIONS

Kim et al., Therapeutic Efficacy—Potentiated and Diseased Organ-Targeting Nanovesicles Derived from Mesenchymal Stem Cells for Spinal Cord Injury Treatment. Nano Lett. Aug. 8, 2018;18(8):4965-4975.

Lee et al., Nanovesicles derived from iron oxide nanoparticles-incorporated mesenchymal stem cells for cardiac repair. Sci Adv. May 1, 2020;6(18):eaaz0952.

Morad et al., Tumor-Derived Extracellular Vesicles Breach the Intact Blood-Brain Barrier via Transcytosis. ACS Nano. Dec. 24, 2019;13(12):13853-13865.

Lai et al., Visualization and tracking of tumour extracellular vesicle delivery and RNA translation using multiplexed reporters. Nat Commun. May 13, 2015;6:7029. doi: 10.1038/ncomms8029.

* cited by examiner

PLATFORM FOR ASSESSMENT OF THE TRANSCYTOSIS OF EXTRACELLULAR VESICLES ACROSS ENDOTHELIAL BARRIERS AND USES THEREOF

RELATED APPLICATIONS

This application is a national stage application under 35 U.S.C. § 371 of International Patent Application No. PCT/US2019/022194, filed Mar. 14, 2019, which claims the benefit under 35 U.S.C. § 119 (e) to U.S. Provisional Application No. 62/643,145, filed Mar. 14, 2018, and entitled "PLATFORM FOR ASSESSMENT OF THE TRANSCYTOSIS OF EXTRACELLULAR VESICLES ACROSS ENDOTHELIAL BARRIERS AND USES THEREOF," the entire contents of each of which are incorporated herein by reference.

FEDERALLY SPONSORED RESEARCH

This invention was made with government support under Grant Number CA185530, awarded by the National Institutes of Health. The Government has certain rights in the invention.

BACKGROUND

More than 90% of cancer-related mortality is due to metastasis. Metastasis to the brain particularly, is associated with very high mortality. Mechanisms driving brain metastasis remain unelucidated. Effective approaches to deliver drugs across the blood brain barrier (BBB) remain to be developed.

SUMMARY

The present disclosure, in some aspects, relate to methods and systems for assessing whether an extracellular vesicles (EV) can cross an endothelial barrier (e.g., the blood brain barrier). In some embodiments, the method may be used to study the underlying mechanisms of cancer metastasis (e.g., brain metastasis). In some embodiments, the methods may be used to predict the efficacy of an EV-based therapeutic or diagnostic agent. In some embodiments, the methods may be used to predict the likelihood of a subject having cancer of developing metastasis (e.g., brain metastasis).

Accordingly, some aspects of the present disclosure provide methods of determining if an extracellular vesicle (EV) crosses the blood brain barrier (BBB), the method comprising:

(i) contacting the EV with a layer of brain endothelial cells cultured on a transwell® insert that divides the transwell® into an upper chamber and a lower chamber, wherein the contacting of the EV with the layer of brain endothelial cells occurs in one of the upper chamber and the lower chamber, and wherein the brain endothelial cells are treated with an agent that increases intracellular cyclic AMP (cAMP) level;

(ii) detecting an EV signal in the other one of the upper chamber and the lower chamber; and (iii) determining the EV signal detected in (ii) is from EVs that crossed the layer of brain endothelial cells via transcytosis.

In some embodiments, the EV is added to the upper chamber and the EV signal is detected in the lower chamber. In some embodiments, the EV is added to the lower chamber and the EV signal is detected in the lower chamber.

In some embodiments, the EV is labeled with a fluorescent molecule or a radioisotope.

In some embodiments, wherein step (iii) comprises comparing the EV signal detected in step (ii) with a control EV signal obtained at a low temperature that inhibits endocytosis, wherein a higher EV signal obtained in step (ii) as compared to the control signal indicates that the EV crosses the BBB via transcytosis. In some embodiments, the low temperature is 0-15° C.

In some embodiments, step (iii) comprises comparing the EV signal detected in step (ii) with a control EV signal obtained from the lower chamber of a control transwell® containing brain endothelial cells that are impaired in endocytosis, wherein a higher EV signal obtained in step (ii) as compared to the control signal indicates that the EV crosses the BBB via transcytosis. In some embodiments, wherein the brain endothelial cells are treated with an agent that inhibits endocytosis. In some embodiments, the agent is selected from the group consisting of: dynasore, Dynoles, Filipin, Chlorpromazine, Monodansylcadaverine, Phenylarsine oxide, Chloroquine, Monensin, Phenothiazines, Methyl-B-cyclodextrin, Cytochalasin D, Amiloride, and Pitstop. In some embodiments, the brain endothelial cells are genetically modified to be defective in endocytic pathway.

In some embodiments, the method further comprises: (iv) determining the EV signal detected in step (ii) is from an intact EV. In some embodiments, step (iv) comprises fractionating EV-containing media by density and determining the signal detected in step (ii) is from a fraction corresponding to EV density. In some embodiments, step (iv) comprises detecting the colocalization of EV signal and an EV biomarker. In some embodiments, the EV biomarker is selected from the group consisting of: CD63, CD9, CD81, Alix, TSG101, Flotillin, Annexins, Integrins. In some embodiments, step (iv) comprises culturing astrocytes and/or pericytes in the lower chamber and determining the uptake of EVs by the astrocytes and/or pericytes.

In some embodiments, the agent that increases intracellular cAMP level is cAMP or an inhibitor of cAMP degradation. In some embodiments, the inhibitor of cAMP degradation degradation comprises a cyclic nucleotide phosphodiesterase inhibitor. In some embodiments, cyclic nucleotide phosphodiesterase inhibitor comprises RO 20-1724.

In some embodiments, the method is carried out at a physiological temperature. In some embodiments, the physiological temperature is 37° C.

In some embodiments, the EV is an exosome, microvesicle, microparticle, ectosome, oncosome, or apoptotic body. In some embodiments, the EV is isolated from a cancer cell. In some embodiments, the cancer cell is a breast cancer cell. In some embodiments, the breast cancer cell is a triple negative breast cancer cell or a HER2+ breast cancer cell.

In some embodiments, the EV is an engineered EV. In some embodiments, the engineered EV encapsulates a drug for the brain. In some embodiments, the drug for the brain is selected from the group consisting of: chemotherapeutic agents, immunotherapeutic agents, and cholinesterase inhibitors.

In some embodiments, the drug is for treating brain metastasis.

In some embodiments, the method is carried out in a high-throughput screening format.

Other aspects of the present disclosure provide methods of determining if an extracellular vesicle (EV) crosses an endothelial barrier, the method comprising:

(i) contacting the EV with a layer of endothelial cells cultured on a transwell® insert that divides the transwell® into an upper chamber and a lower chamber, wherein the contacting of the EV with the layer of endothelial cells occurs in one of the upper chamber and the lower chamber, and wherein the brain endothelial cells are treated with an agent that increases intracellular cyclic AMP (cAMP) level;

(ii) detecting an EV signal in the other one of the upper chamber and the lower chamber; and (iii) determining the EV signal detected in (ii) is from EVs that crossed the layer of endothelial cells via transcytosis.

In some embodiments, the endothelial cells are brain endothelial cells, lung endothelial cells, gastrointestinal endothelial cells, bone marrow endothelial cells, or renal endothelial cells. In some embodiments, the endothelial cells are brain endothelial cells. In some embodiments, the brain endothelial cells are treated with an agent that increases intracellular cyclic AMP (cAMP) level. In some embodiments, the endothelial cells are lung endothelial cells. In some embodiments, the lung endothelial cells are treated with an inflammatory agent. In some embodiments, the endothelial cells are bone marrow endothelial cells. In some embodiments, the bone marrow endothelial cells are treated with an inflammatory cytokine. In some embodiments, the endothelial cells are renal endothelial cells. In some embodiments, the renal endothelial cells are treated with an inflammatory cytokine. In some embodiments, the endothelial cells are gastrointestinal endothelial cells. In some embodiments, the gastrointestinal endothelial cells are treated with an inflammatory cytokine. In some embodiments, the inflammatory cytokine is selected from the group consisting of: interleukin 1 (IL-1), IL-6, NACHT, LRR and PYD domains-containing protein 3 (NLRP3), tumor necrosis factor (TNF), IL-8, and IL-18.

Further provided herein are methods of determining the likelihood of brain metastasis of a cancer cell, the method comprising determining if an extracellular vesicle (EV) isolated from the cancer cell can cross the blood brain barrier (BBB) using the method described herein, wherein the cancer cell is determined to have high likelihood of brain metastasis if the EV can cross the BBB, and wherein the cancer cell is determined to have low likelihood of brain metastasis if the EV cannot cross the BBB.

In some embodiments, the cancer is selected from the group consisting of: breast cancer, lung cancer, melanoma, colorectal cancer, and pancreatic cancers. In some embodiments, the cancer is breast cancer. In some embodiments, the breast cancer is triple negative breast cancer or HER2+ breast cancer.

In some embodiments, the cancer cell is cultured in vitro. In some embodiments, the cancer cell is isolated from a subject. In some embodiments, the method further comprises treating the subject to reduce the likelihood of brain metastasis if the EV isolated from the cancer cell can cross the BBB.

Other aspects of the present disclosure provide methods of reducing the likelihood of a subject having cancer from developing brain metastasis, the method comprising isolating an extracellular vehicle (EV) from the subject, determining if the EV can cross the blood brain barrier (BBB) using the method described herein, and administering to the subject an effective amount of an anti-cancer drug to reduce the likelihood of brain metastasis.

In some embodiments, the method further comprises subjecting the subject to a second method of diagnosing brain metastasis. In some embodiments, the second method is computed tomography (CT) or magnetic resonance imaging (MRI).

In some embodiments, wherein the anti-cancer drug is Neratinib or lapatinib.

In some embodiments, the cancer is selected from the group consisting of: breast cancer, lung cancer, melanoma, colorectal, and pancreatic cancer. In some embodiments, the cancer is breast cancer. In some embodiments, the breast cancer is triple negative breast cancer or HER2+ breast cancer.

In some embodiments, the anti-cancer drug is administered orally, intravenously, intramuscularly, subcutaneously, or intrathecally. In some embodiments, comprising administering to the subject an effective amount of a second anti-cancer agent.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. In the drawings, each identical or nearly identical component that is illustrated in various FIGS. is represented by a like numeral. For purposes of clarity, not every component may be labeled in every drawing.

In the drawings:

(FIG. 1A) Treatment of the brain endothelial cells with cAMP significantly increased the expression of the tight junction molecule, ZO-1. The apparent permeability coefficient of Fluorescein Dextran (70 KDa) (FIG. 1B) and Sodium Fluorescein (376 Da) (FIG. 1C) was decreased within 1 and 4 days, respectively.

(FIG. 5A) The media collected from the lower chamber in the transcytosis assay should be added on top of a density gradient for ultracentrifugation. (FIG. 5B) EVs added directly on the gradient mostly end up in the 10, 15, and 25% fractions. (FIG. 5C) The transcytosis assay demonstrates a peak at 25% fraction, demonstrating that EVs are the source of part of the signal in the lower chamber (Luciferase-labeled EVs were used for this experiment).

(FIG. 8A) TdTomato exosomes are taken up by brain ECs and brain cells beyond the BBB (white arrows). (FIG. 8B) Time-lapse imaging demonstrates evidence suggesting that endocytic vesicles containing exosomes can fuse with the plasma membrane (white arrows).

(FIG. 10A) Exosome were isolated from the MDA-MB-231 parental, brain-seeking and bone-seeking cells using a sequential centrifugation technique. (FIG. 10B) Exosomes were positive for exosome markers Alix, CD63, and CD9 and were negative for the Golgi marker GM130, shown by western blot. (FIG. 10C) The median size of the exosomes was 145-155 nm, measured by nanoparticle tracking analysis. (FIG. 10D) By electron microscopy, exosomes look round in shape and heterogeneous in size.

DETAILED DESCRIPTION OF CERTAIN EMBODIMENTS

Figure 1A:
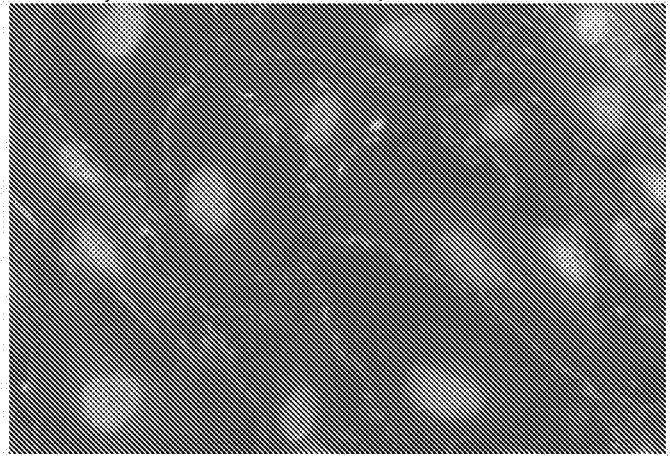
FIGS. 1A to 1C. Development of an in vitro BBB model.
Figure 1A:
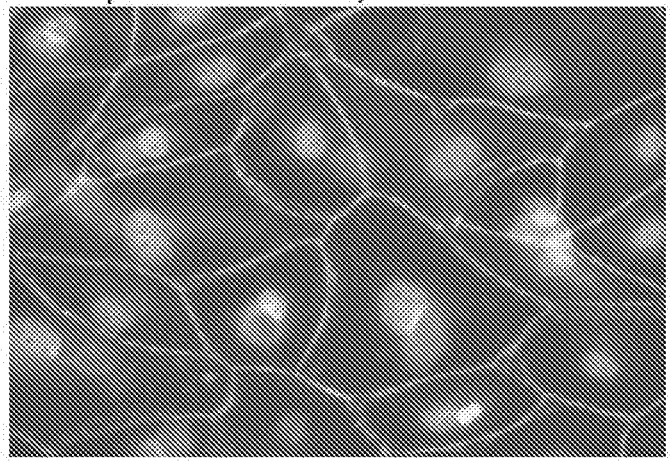

To date, the interactions between extracellular vesicles (EVs) with the blood brain barrier are mostly studied using a Transwell® model that is based on cultivation of brain endothelial cells on filters to mimic the endothelial monolayer in the blood brain barrier (BBB) (e.g., as described in Chen C, et al., Cell Mol Bioeng. 2016 December; 9(4):509-529, incorporated herein by reference). However, this model does not recapitulate the integrity of the BBB, as brain endothelial cells lose their unique junctional features in in vitro cultures. Consequently, the results generated using a traditional Transwell® cannot be extended to the real BBB, thus diminishing their value in facilitating the development of novel therapeutics and/or diagnostics. The challenge with the BBB is also extended to any other types of endothelial barriers (e.g., lung endothelial barrier or gastrointestinal endothelial barrier).

Accordingly, described herein, in some aspects, is an in vitro platform that more reliably recapitulates the in vivo integrity of an endothelial barrier (e.g., BBB, lung endothelial barrier or gastrointestinal endothelial barrier). In some embodiments, such an in vitro platform can be used to assess whether an EV can cross the specified endothelial barrier (e.g., to deliver a therapeutic agent or diagnostic agent across such endothelial barrier to a target site). In some embodiments, multiple controls are included in the in vitro platform to insure an accurate assessment. In some embodiments, this platform described herein can be used for comprehensive and precise determination of the interactions of EVs with different endothelial barriers (e.g., the BBB) in a variety of pathological conditions. In some embodiments, the pathological condition is cancer (e.g., primary and metastatic brain cancer), neurodegenerative and neurodevelopmental diseases (e.g., Alzheimer's, Parkinson's, and autism), vascular disorders (e.g., cerebrovascular accidents such as well stroke, or trauma), and infection-related diseases. In some embodiments, the platform described herein has applications in the context of biomedical research, therapeutics development, and diagnostics development.

The EVs cross the endothelial barrier via transcytosis. "Transcytosis" is a type of transcellular transport in which various macromolecules are transported across the interior of a cell. Macromolecules (e.g., nucleic acids, proteins, or EVs) are captured in vesicles on one side of the cell, drawn across the cell, and ejected on the other side. While transcytosis is most commonly observed in cells of an epithelium or endothelium, the process is also present elsewhere.

The platform described herein uses a Transwell®. A "transwell®" refers to a well (e.g., a cell culture well) into which an insert (referred herein to as "transwell® insert") can be placed to divide the well into two chambers, a first chamber and a second chamber. The transwell® insert comprises a membrane filter onto which cells can be cultured. The membrane filter may be of different chemical compositions and/or properties. Transwell® inserts with membrane filters of different chemical compositions and/or properties are commercially available (e.g., from Thermo Scientific). One skilled in the art can choose the type of transwell® inserts with appropriate membrane filters suitable for his/her specific purpose.

As described herein, the endothelial cells cultured on the membrane filter of the transwell® insert are treated with appropriate agents such that the cells recapitulate the in vivo integrity of an endothelial barrier. The endothelial cells may be any endothelial cells that form endothelial barriers in the body. Treatment methods differ based on the endothelial cells cultured. In some embodiments, the endothelial cells are brain endothelial cells, lung endothelial cells, gastrointestinal endothelial cells, bone marrow endothelial cells, or renal endothelial cells.

In some embodiments, the endothelial cells cultured on the membrane filter of the transwell® insert are brain endothelial cells treated with an agent that increases intracellular cyclic AMP (cAMP) level. Brain endothelial cells form the blood brain barrier (BBB). The BBB is a highly selective semipermeable membrane barrier that separates the circulating blood from the brain and extracellular fluid in the central nervous system (CNS). The BBB allows the passage of water, some gases, and lipid-soluble molecules by passive diffusion, as well as the selective transport of molecules such as glucose and/or amino acids that are crucial to neural function. Brain endothelial cells that make up the BBB restrict the diffusion of microscopic objects (e.g., bacteria) and large or hydrophilic molecules (e.g., nucleic acids and hydrophilic proteins) into the cerebrospinal fluid (CSF).

Brain endothelial cells cultured in vitro lose their unique junctional features and do not recapitulate in vivo conditions (e.g., as described in He et al., Stroke. 2014 August; 45(8): 2514-2526, incorporated herein by reference). Treating in vitro cultured brain endothelial cells with an agent that increases intracellular cAMP level promote the cells to form high resistance tight junctions that exhibit low rates of paracellular leakage and fluid-phase endocytosis (e.g., as described in Rubin et al., The Journal of Cell Biology, vol. 115, No. 6, 1725-1735, 1991, incorporated herein by reference). The brain endothelial cells may be cultured in any appropriate media for brain cells. In some embodiments, the brain endothelial cells are cultured in astrocyte-conditioned media.

An "agent that increases intracellular cAMP level" refers to an agent that, upon contacting the brain endothelial cell(s), results in an increase in the intracellular cAMP level by at least 20%, relative to without the agent. For example, the agent may result in an increase in the intracellular cAMP level by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or more, relative to without the agent. In some embodiments, the agent results in an increase in the intracellular cAMP level by 20%, 30%, 40%, 50%, 60%, 70%, 80%, 90%, 100%, 2-fold, 5-fold, 10-fold, 100-fold, 1000-fold, or more, relative to without the agent.

In some embodiments, the agent is cAMP. In some embodiments, the agent is an inhibitor of cAMP degradation. An "inhibitor of cAMP degradation" refers to an agent that prevents cAMP from being degraded via any intracellular mechanisms. In some embodiments, the inhibitor of cAMP degradation reduces cAMP degradation by at least 20%, relative to without the inhibitor. For example, the inhibitor of cAMP degradation may reduce cAMP degradation by at least 20%, at least 30%, at least 40%, at least 50%, at least 60%, at least 70%, at least 80%, at least 90%, or 100%, relative to without the inhibitor. In some embodiments, the inhibitor of cAMP degradation reduces cAMP degradation by 20%, 30%, 40%, 50%, 60%, 70%, 80%, 90%, or 100%, relative to without the inhibitor. In some embodiments, the inhibitor of cAMP degradation is an inhibitor of cyclic nucleotide phosphodiesterase. In some embodiments, the inhibitor of cAMP is RO 20-1724. RO 20-1724 is commercially available, e.g., from Tocris Biosciences (Catalog No. 0415).

In some embodiments, the brain endothelial cells are cultured on the membrane filter of the transwell® insert until confluency prior to treating with the agent that increases intracellular cAMP level. In some embodiments, the brain endothelial cells are cultured on the membrane filter of the transwell® insert for 48-72 hours (e.g., 48 hours, 54 hours, 60 hours, 66 hours, or 72 hours) prior to treating with the agent that increases intracellular cAMP level. In some embodiments, the brain endothelial cells are treated for at least 1 hour (e.g., at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 24 hours, at least 36 hours, at least 48 hours, at least 60 hours, at least 72 hours, at least 84 hours, at least 96 hours, at least 100 hours, or longer) before being used in the methods described herein.

Other types of endothelial cells may also be used in the platform and methods described herein. Methods of conditioning other types of endothelial cells such that they recapitulate the endogenous condition of the respective endothelial barrier are described in the art, e.g., in Ohmura et al, Mol Biol Cell. 2017 Jun. 15; 28(12):1622-1635; Prendergast et al, Haematologica. 2017 March; 102(3):445-453; Kumar et al, Semin Nephrol. 2015 January; 35(1): 96-107; and Cromer et al, World J Gastroenterol. 2011 Feb. 7; 17(5): 578-593, incorporated herein by reference.

In some embodiments, the endothelial cells cultured on the membrane filter of the transwell® insert are lung endothelial cells. In some embodiments, the lung endothelial cells are treated with an inflammatory cytokine. In some embodiments, the endothelial cells cultured on the membrane filter of the transwell® insert are gastrointestinal endothelial cells. In some embodiments, the gastrointestinal endothelial cells are treated with an inflammatory cytokine. In some embodiments, the endothelial cells cultured on the membrane filter of the transwell® insert are bone marrow endothelial cells. In some embodiments, the bone marrow endothelial cells are treated with an inflammatory cytokine. In some embodiments, the endothelial cells cultured on the membrane filter of the transwell® insert are renal endothelial cells. In some embodiments, the renal endothelial cells are treated with an inflammatory cytokine. Exemplary inflammatory cytokines include, without limitation: interleukin 1 (IL-1), IL-6, NACHT, LRR and PYD domains-containing protein 3 (NLRP3), tumor necrosis factor (TNF), IL-8, and IL-18.

Different types of extracellular vesicles (EVs) may be tested using the methods described herein. "Extracellular vesicles" are a heterogeneous group of cell-derived membranous structures that originate from the endosomal system or are shed from the plasma membrane of cells. EVs are present in biological fluids and are involved in multiple physiological and pathological processes. Non-limiting examples of EVs include: exosomes, microvesicles, microparticles, ectosomes, oncosomes, and apoptotic bodies.

An "exosome" is a cell-derived vesicle that is present in many eukaryotic fluids, including blood, urine, and cultured medium of cell cultures. A "microvesicle" is a circular fragment of plasma membrane ranging from 100 nm to 1000 nm shed from almost all cell types. A "microparticle" is a particle between 0.1 and 100 m in size. Commercially available synthetic microparticles are available in a wide variety of materials, including ceramics, glass, polymers, and metals. An "ectosome" is a large vesicle (e.g., ranging from 100-1000 nm in diameter) assembled at and released from the plasma membrane through outward protrusion or budding. An "oncosome" is an EV that plays a role in cancer cell intercellular communication and contributes to the reprogramming of normal cells. An "apoptotic body" is a vesicle containing parts of a dying cell. Apoptotic bodies can be formed during the execution phase of the apoptotic process, when the cell's cytoskeleton breaks up and causes the membrane to bulge outward.

In some embodiments, an EV is isolated from cultured cells (e.g., cultured cancer cells). In some embodiments, the cancer cells are breast cancer cells (e.g., HER2+ breast cancer cells or triple negative breast cancer cells). In some embodiments, the cancer cells are from a human subject. In some embodiments, the EV is a synthetic or engineered EV (e.g., as described in Sasso et al., Microcirculation. 2017 January; 24(1) and Smith et al., Biogerontology. 2015 April; 16(2): 147-185, incorporated herein by reference).

EVs can be used as drug carriers (e.g., as described in Alvarez-Erviti et al., Nature Biotechnology, volume 29, number 4, 341-347, 2011; and Yang et al., Pharm Res. 2015 June; 32(6): 2003-2014, incorporated herein by reference). Thus, in some embodiments, the EVs of the present disclosure encapsulate a drug. In some embodiments, the drug is a drug for the brain (e.g., chemotherapeutic agents, immunotherapeutic agents, drugs for treating neuronal disorders, and cholinesterase inhibitors).

Any of the chemotherapeutic agents or immunotherapeutic agents (e.g., immune checkpoint inhibitors) described herein or known in the art may be encapsulated in an EV for delivery to the brain. An acetylcholinesterase inhibitor (AChEI) is a chemical or a drug that inhibits the acetylcholinesterase enzyme from breaking down acetylcholine, thereby increasing both the level and duration of action of the neurotransmitter acetylcholine. Suitable cholinesterase inhibitors include, without limitation: Physostigmine, Neostigmine, Pyridostigmine, Ambenonium, Demecarium, Rivastigmine, Phenanthrene derivatives (e.g., Galantamine), Caffeine, Rosmarinic acid, Alpha-Pinene, Piperidines, Donepezil, Tacrine, Edrophonium, Huperzine A, Ladostigil, Ungeremine, Lactucopicrin, Acotiamide, Echothiophate, Diisopropyl fluorophosphate, Cadusafos, Chlorpyrifos, Cyclosarin, Dichlorvos, Dimethoate, Metrifonate, Sarin, Soman, Tabun, VX, VE, VG, VM, Diazinon, Malathion, Parathion, Aldicarb, Bendiocarb, Bufencarb, Carbaryl, Carbendazim, Carbetamide, Carbofuran, Carbosulfan, Chlorbufam, Chloropropham, Ethiofencarb, Formetanate, Methiocarb, Methomyl, Oxamyl, Phenmedipham, Pinmicarb, Pirimicarb, Propamocarb, Propham, Propoxur, Onchidal and Coumarins. In some embodiments, the drug is for treating brain cancer (e.g., primary brain cancer or brain metastasis).

Assessing whether an EV encapsulating a drug can cross an endothelial barrier (e.g., the BBB) can provide information as to whether the drug is likely to be delivered across the endothelial barrier to its target site.

In some embodiments, the EVs of the present disclosure is labeled with a detectable molecule such that its crossing the endothelial barrier can be observed and/or quantified. For example, the EVs are labeled with a fluorescent dye. Any known and/or commercially available fluorescent dyes may be used. One skilled in the art is familiar with choosing fluorescent dyes. In some embodiments, the EV is labeled with a fluorescent protein, e.g., a palmitoylated GFP or a tandem-dimer Tomato. In some embodiments, the fluorescent protein is associated with the membrane of the EV (e.g., via an attached lipid). In some embodiments, the cells where the EVs are isolated from are transfected with membrane-bound labels to produce labeled EVs (instead of labeling isolated EVs in vitro). Such methods have been described in Lai et al., Nat Commun, 2015. 6: p. 7029, incorporated herein by reference. In some embodiments, the EVs are labeled with a radioisotope. One skilled in the art is familiar with methods of isotopic labeling. In a non-limiting example, radioisotope labeled lipids or amino acids can be added to the culture media for the cells where EVs are isolated from to produce labeled EVs, e.g., as described in Varga et al., Cancer Biother Radiopharm. 2016 June; 31(5): 168-73, incorporated herein by reference. In some embodiments, the EVs are labeled with an enzyme that can produce luminescence upon contacting a substrate (e.g., luciferase).

To determine whether the EV can cross an endothelial barrier (e.g., BBB), the EVs are contacted with the endothelial cells (e.g., brain endothelial cells) cultured on the membrane filter of the transwell® insert. In some embodiments, EVs are added to one of the two chambers (the upper chamber or the lower chamber) of the transwell® such that the EV signals are detected in the other chamber of the transwell®.

Transcytosis can occur bidirectionally, depending on the type of endothelial barrier and the properties of the EV. In the transwell®, EVs can be taken up by cells from the abluminal side (lower chamber) and be transcytosed to the luminal side (upper chamber), or vice versa. Thus, in some embodiments, the EV is added to the upper chamber and the EV signal is detected in the lower chamber. In some embodiments, the EV is added to the lower chamber and the EV signal is detected in the upper chamber.

One skilled in the art is familiar with how to detect the EV signal in the chamber where the EVs are moving to via transcytosis (can be either the upper chamber or the lower chamber). The detection methods may depend how the EVs are labeled (e.g., fluorescence, radioisotope, etc.). In some embodiments, the detection can be done by assaying for EV specific markers (e.g., via ELISA).

In some embodiments, the method described herein is carried out at a temperature between 16-40° C. (e.g., 16-40° C., 16-35° C., 16-30° C., 16-25° C., 16-20° C., 20-40° C., 20-35° C., 20-30° C., 20-25° C., 25-40° C., 25-35° C., 25-30° C., 30-40° C., 30-35° C., or 35-40° C.). In some embodiments, the method is carried out at room temperature, e.g., 25° C. In some embodiments, the method is carried out at a physiological temperature, e.g., 37° C.

Some EVs may be able to cross the layer of endothelial cells (e.g., brain endothelial cells) via passive paracellular transport, creating false positive signals. Thus, in some aspects, the methods described herein further comprise determining that the EV signals detected in the chamber where the EVs are moving into are from EVs that crossed the layer of epithelial cells (e.g., brain epithelial cells) via transcytosis. In some embodiments, this can be achieved by comparing the signal detected in the chamber where the EVs are moving into with a control signal obtained from a control experiment where endocytosis of the cultured endothelial cells is impaired. "Endocytosis" is a form of active transport in which a cell transports molecules (e.g., nucleic acids, proteins, or EVs) through the hydrophobic plasma or cell membrane into the cell by engulfing them in an energy-using process.

In some embodiments, being "impaired in endocytosis" means that the number of endothelial cells that have the ability for endocytosis is reduced by at least 20% (e.g., by at least 20%, at least 30%, at least 40%, at least 50%, at least 60%, at least 70%, at least 80%, at least 90%, or 100%), relative to endothelial cells that are not impaired in endocytosis. In some embodiments, being "impaired in endocytosis" means that the time needed for the impaired endothelial cells for endocytosis is prolonged by at least 20% (e.g., by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or more), relative to endothelial cells that are not impaired in endocytosis. Inhibition of endocytosis also inhibits transcytosis.

In some embodiments, endocytosis of the cultured endothelial cells used in the control experiment is inhibited by low temperature. For example, the control experiment may be carried out at 0-15° C. In some embodiments, the control experiment is carried out at 0-15° C., 0-10° C., 0-5° C., 5-15° C., 5-10° C., or 10-15° C. In some embodiments, the control experiment is carried out at 0° C., 1° C., 2° C., 3° C., 4° C., 5° C., 6° C., 7° C., 8° C., 9° C., 10° C., 11° C., 12° C., 13° C., 14° C., or 15° C.

In some embodiments, endocytosis of the cultured endothelial cells used in the control experiment is inhibited by treating the endothelial cells with an agent that inhibits endocytosis. Non-limiting examples of agents that inhibit endocytosis include: dynasore, Dynoles, Filipin, Chlorpromazine, Monodansylcadaverine, Phenylarsine oxide, Chloroquine, Monensin, Phenothiazines, Methyl-B-cyclodextrin, Cytochalasin D, Amiloride, and Pitstop.

In some embodiments, endocytosis of the cultured endothelial cells used in the control experiment is inhibited because the endothelial cells are genetically modified such that it is defective in the endocytic pathway. For example, the cells may lack or have reduced expression of a factor (e.g., protein) that is required for endocytosis. In some embodiments, the factor (e.g., protein) required for endocytosis is selected from the group consisting of ecaveolin 1, clathrin, rab proteins, Rac1, and CDC42 (e.g., as described in Verdera et al, Journal of Controlled Release 266 (2017) 100-108, incorporated herein by reference). One skilled in the art is familiar with methods of genetic modification. Any known genetic modification/engineering methods may be used.

In some embodiments, it can be determined that the EVs crossed the endothelial barrier via transcytosis, if the signal detected in the chamber where the EVs are moving into is higher than the control signal (e.g., at least 20%, at least 30%, at least 40%, at least 50%, at least 60%, at least 70%, at least 80%, at least 90%, at least 100%, at least 2-fold, at least 5-fold, at least 10-fold, at least 100-fold, or at least 1000-fold higher). In some embodiments, it can be determined that the EVs crossed the endothelial barrier via transcytosis, if no signal is detected in the control experiments, and a signal is detected in the chamber where the EVs are moving into.

In some embodiments, the method(s) described herein further comprise(s) determining the EV signal detected in the chamber where the EVs are moving into is from intact EVs. An "intact EV" means an EV that is structurally complete and/or functionally competent. This can be achieved in several different ways. In some embodiments, the EV-containing media from the chamber where the EVs are moving into is collected and fractionated by density. For example, the media may be subjected to ultracentrifugation on top of a sucrose or Iodixanol density gradient. The EVs can move through the gradient until it reaches a gradient corresponding to its density. Fractions in the range of EV densities can be identified by detecting EV associated markers and collected for EV signal detection (e.g., fluorescence or luminescence). It can be determined that the EV signals are, at least partially, from intact EVs if EV signals can be detected in the EV fraction.

In some embodiments, colocalization of EV signals and EV biomarkers indicate that the EV signal detected in the chamber where the EVs are moving into is from intact EVs. Suitable EV markers that can be detected include, without limitation: CD63, CD9, CD81, Alix, TSG101, Flotillin, Annexins, Integrins. EV biomarkers can be detected via any known methods in the art, e.g., immunostaining.

In some embodiments, to determine that the EV signals are from intact EVs, cells can be cultured (e.g., on a cover slip) in the chamber where the EVs are moving into (can be either the upper chamber or the lower chamber). Intact EVs that cross the endothelial barrier can enter these cells via endocytosis. These cells can then be processed (e.g., fixed) for intracellular EV detection. In some embodiments, when the endothelial barrier is a layer of brain endothelial cells, astrocytes and/or pericytes are cultured in the chamber wherein the EVs are moving into.

In some embodiments, the method is carried out in a high throughput format. For example, in some embodiments, the transwells® are in a multi-well format (e.g., 24-96 well), wherein each well can be used to assess the transcytosis ability of one type of EV. Using this format, multiple types of EVs from different origins or with different features with different transcytosis ability through the same endothelial barrier can be assessed. In some embodiments, in each well, a different type of endothelial cells may be cultured on the membrane insert of the transwell® insert. Thus, an EV's transcytosis ability through different endothelial barriers may be assessed.

It is also described herein that the transcytosis ability of EVs originating from cancer cells (e.g., breast cancer cells) can be used to predict the likelihood of metastasis. For example, if an EV originated from a cancer cell is determined using the methods described herein to be able to cross an endothelial barrier (e.g., the BBB), there is a higher likelihood of such cancer to metastasize to the respective organ (e.g., the brain). Accordingly, other aspects of the present disclosure provide methods of determining the likelihood of metastasis (e.g., brain metastasis) of a cancer cell, the methods comprising determining if an EV isolated from the cancer cell can cross an endothelial barrier (e.g., the BBB) using the described herein, wherein the cancer cell is determined to have high likelihood of metastasis (e.g., brain metastasis) if the EV can cross the endothelial barrier (e.g., the BBB), and wherein the cancer cell is determined to have low likelihood of metastasis (e.g., brain metastasis) if the EV cannot cross the endothelial barrier (e.g., the BBB).

In some embodiments, if an EV originating from a cancer cell is determined to be able to cross an endothelial barrier (e.g., the BBB) using the methods described herein, the cancer has a higher likelihood (e.g., at least 20% higher) of metastasizing to the respective organ (e.g., the brain). For example, the cancer may have a likelihood that is at least 20%, at least 30%, at least 40%, at least 50%, at least 60%, at least 70%, at least 80%, at least 90%, at least 100%, at least 2-fold, at least 5-fold, at least 10-fold, at least 100-fold, or at least 1000-fold higher than a cancer cell that is determined to not be able to cross the endothelial barrier (e.g., the BBB). In some embodiments, the cancer has a likelihood that is 20%, 30%, 40%, 50%, 60%, 70%, 80%, 90%, 100%, 2-fold, 5-fold, 10-fold, 100-fold, or 1000-fold higher than a cancer cell that is determined to not be able to cross the endothelial barrier (e.g., the BBB).

The present disclosure also, in some aspects, provide characterization of EVs originated from cancer cells (e.g., breast cancer cells). Proteomic analysis identified proteins that are differentially presented in EVs originated from cancer cells that metastasize (e.g., to the brain), relative to EVs originated from cancers cells that do not metastasize. Proteins that are over-represented in EVs originated from cancer cells that metastasize (e.g., breast cancer cells that metastasize to the brain) include, without limitation: moesin, annexin A2 and A6, urokinase clusterin, integrin alpha plasminogen activator receptor (UPAR), brain acid soluble protein 1, 2, and 3, and actin. Detection of one of more (e.g., 1, 2, 3, 4, 5, or more) of these proteins in EVs can also be used to predict whether the cancer cells from which the EVs originated are likely to metastasize (e.g., to the brain).

The EV may originate from any type of cancer cell. In some embodiments, the EV is from breast cancer cells, lung cancer cells, melanoma cells, colorectal cancer cells, or pancreatic cancer cells. In some embodiments, the EV is from breast cancer cells (e.g., triple negative breast cancer cells or HER2+ breast cancer cells. In some embodiments, the cancer cells are cultured in vivo. In some embodiments, the cancer cells are isolated from a subject. In some embodiments, the EV is isolated from a bodily fluid of a subject. In some embodiments, the EV is isolated from the subject's serum, plasma, urine, cerebrospinal fluid, or saliva.

In some embodiments, the method further comprises treating the subject who has cancer, and whose cancer cells produced EVs that are determined to have high likelihood to metastasize. As such, other aspects of the present disclosure provide methods of reducing the likelihood of a subject having cancer from developing metastasis (e.g., brain metastasis), the method comprising isolating an extracellular vehicle (EV) from the subject, determining if the EV can cross the blood brain barrier (BBB) using the method described herein, and administering to the subject an effective amount of an anti-cancer drug to reduce the likelihood of metastasis (e.g., brain metastasis).

In some embodiments, subjects who are determined to have high likelihood of developing metastatic cancer (e.g., brain metastasis) are treated for the metastatic cancer. In some embodiments, the subject is subjected to a second diagnostic methods to determine whether metastatic cancer (e.g., brain metastasis) has developed. Any cancer diagnostic methods may be used, e.g., tomography (CT) or magnetic resonance imaging (MRI). In some embodiments, the subject has metastatic cancer (e.g., brain metastasis) and is treated for the metastatic cancer (e.g., brain metastasis). In some embodiments, the subject has not yet developed metastatic cancer (e.g., brain metastasis) and is treated prophylactically for the metastatic cancer (e.g., brain metastasis).

Any anti-cancer agent may be used. In some embodiments, one or more types (e.g., 1, 2, 3, 4, 5 types or more) of anti-cancer agents are used. In some embodiments, the anti-cancer agent is selected from the group consisting of: small molecules, oligonucleotides, polypeptides, and combinations thereof. In some embodiments, the anti-cancer agent is a chemotherapeutic agent. In some embodiments, the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In some embodiments, the anti-cancer agent is an immune checkpoint inhibitor. An "immune checkpoint" is a protein in the immune system that either enhances an immune response signal (co-stimulatory molecules) or reduces an immune response signal. Many cancers protect themselves from the immune system by exploiting the inhibitory immune checkpoint proteins to inhibit the T cell signal. Exemplary inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GALS), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3), and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reducing the immune response.

An "immune checkpoint inhibitor" is a molecule that prevents or weakens the activity of an immune checkpoint protein, For example, an immune checkpoint inhibitor may inhibit the binding of the immune checkpoint protein to its cognate binding partner, e.g., PD-1, CTLA-4, or A2aR. In some embodiments, the immune checkpoint inhibitor is a small molecule. In some embodiments, the immune checkpoint inhibitors is a nucleic acid aptamer (e.g., a siRNA targeting any one of the immune checkpoint proteins). In some embodiments, the immune checkpoint inhibitor is a recombinant protein. In some embodiments, the immune checkpoint inhibitor is an antibody. In some embodiments, the antibody comprises an anti-CTLA-4, anti-PD-1, anti-PD-L1, anti-TIM3, anti-LAG3, anti-B7-H3, anti-B7-H4, anti-BTLA, anti-GALS, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (Keytruda®) or nivolumab (Opdivo®) and the anti-CTLA-4 antibody is ipilimumab (Yervoy®). Thus, in some embodiments, the immune checkpoint inhibitor comprises pembrolizumab, nivolumab, ipilimumab, or any combination of two or more of the foregoing antibodies. The examples described herein are not meant to be limiting and that any immune checkpoint inhibitors known in the art and any combinations thereof may be used in accordance with the present disclosure. In some embodiments, the anti-cancer agent is for treating brain metastasis. In some embodiments, the anti-cancer agent for treating brain metastasis is meratinib or lapatinib.

In some embodiments, more than one anti-cancer agents are used. For example, the subject may be administered one anti-cancer agent, and further administered a second anti-cancer agent. Any combination of the anti-cancer agents described herein or known in the art may be used. One skilled in the art is able to choose the appropriate anti-cancer agents to use.

"A therapeutically effective amount" as used herein refers to the amount of each therapeutic agent (e.g., anti-cancer agent) of the present disclosure required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the anti-cancer agent used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the anti-cancer agent (such as the half-life of the anti-cancer agent, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the anti-cancer agent is administered for preventive or therapeutic purposes, previous therapy, the subject's clinical history and response to the antagonist, and the discretion of the attending physician. Typically the clinician will administer an anti-cancer agent until a dosage is reached that achieves the desired result. Administration of one or more anti-cancer agents can be continuous or intermittent, depending, for example, upon the recipient's physiological condition, whether the purpose of the administration is therapeutic or prophylactic, and other factors known to skilled practitioners. The administration of an anti-cancer agent may be essentially continuous over a preselected period of time or may be in a series of spaced dose, e.g., either before, during, or after developing a disease.

As used herein, the term "treating" refers to the application or administration of an anti-cancer agent to a subject in need thereof. "A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., rodent (e.g., mouse or rat), primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). The non-human animal may be a male or female at any stage of development. The non-human animal may be a transgenic animal or genetically engineered animal.

In some embodiments, the subject is a companion animal (a pet). "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., rats, mice, guinea pigs, and hamsters), rabbits, or non-human primates.

In some embodiments, a "subject in need thereof" refers to a subject that needs treatment of cancer (e.g., metastatic cancer). In some embodiments, the subject has or is at risk of developing metastatic cancer (e.g., brain metastasis).

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

Conventional methods, known to those of ordinary skill in the art of medicine, can be used to administer the anti-cancer agent the subject, depending upon the type of disease to be treated or the site of the disease. The anti-cancer agent can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1

Platform for Assessment of the Transcytosis of Extracellular Vesicles Across the Blood Brain Barrier and Uses Thereof The blood brain barrier (BBB) is a complex structure consisting of brain endothelial cells, astrocytes and brain microvascular pericytes that together form a highly selective barrier, which only allows for passive paracellular transport of molecules smaller than 400 Da. The BBB is the major limiting factor that has led to the inefficiency of current therapeutic approaches for brain disorders and the absence of reliable biomarkers [1]. Studies have shown that extracellular vesicles (EVs) which are around 1000 KDa or larger in size, can cross the BBB via transcellular transport. EVs play diverse roles in the progress of pathologies including those associated with the nervous system (e.g. brain tumors, neurodegenerative diseases such as Alzheimer's and Parkinson, etc.) and hold great promise as potential diagnostic biomarkers and therapeutic modalities [2]. It is therefore of great interest to assess the interactions of EVs with the BBB. The characteristics and complexity of EVs have been taken into consideration and a platform has been developed that allows for reliable assessment of the process of transcytosis of EVs across the BBB and the mechanisms involved in this process. This platform has the potential to pave the way towards development of novel EV-based therapeutic and diagnostic approaches for brain disorders.

Labeling of the Etracellular Vesicles:

For the purpose of assessing transcytosis, it is critical that no free dye/label remains in the EV suspension during the labeling process. To achieve this, the cells of interest are transfected with membrane-bound labels to produce labeled EVs. The current state-of-the-art labeling approaches for EVs include membrane-bound palmitoylated GFP or Tandem-dimer Tomato (TdTomato), developed at the Mass General Hospital [3]. Cells of interest, transfected with these constructs, produce indirectly-labeled EVs that fluoresce brightly and can be evaluated using a fluorescent microscope or fluorescence plate reader. Unlike direct EV dyes such as PKH67, DiR, etc., these labeling approaches do not contaminate labeled EVs with free dye, which often remains a problem regardless of the rigorousness of the washing procedures and as a result are superior for the purpose of EV transcytosis studies.

Figure 1B:
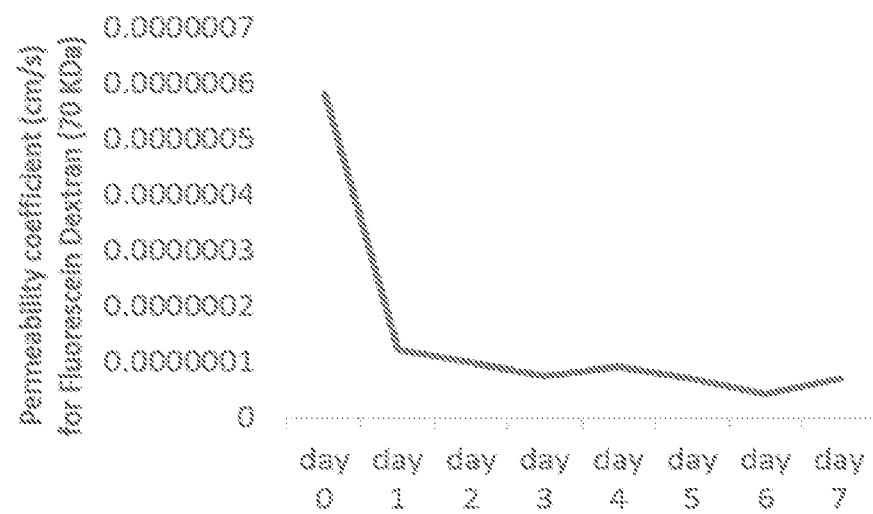
Figure 1C:
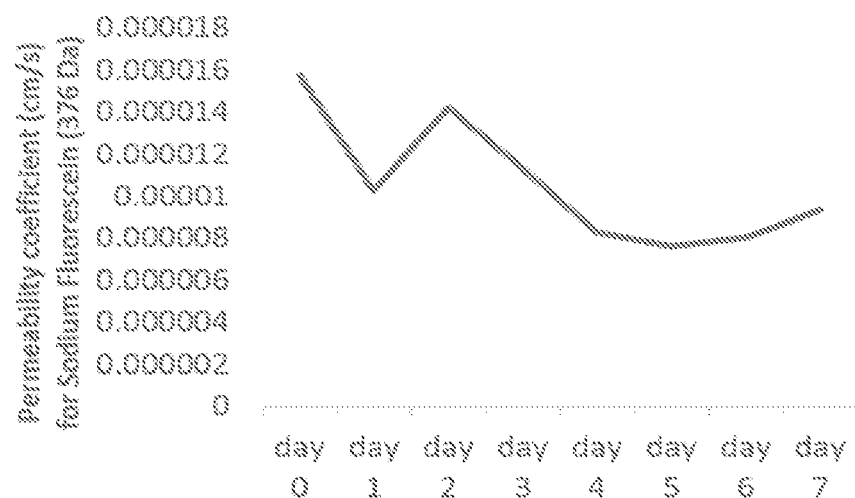

Description of the Blood-Brain-Barrier Model:

Endothelial cells in brain have high expression of tight junctions and adherence junctions that provides a barrier with limited permeability. However, when cultured in vitro, brain endothelial cells mostly lose these functional features, which significantly increases the permeability of brain EC monolayer. As a result, simple culture of these cells on transwell® filters does not provide a reliable model for studying transcytosis of macromolecules. The loss of junctional features is also most prominent for human primary brain endothelial cells. While the culture of murine or porcine endothelial cells on transwell® filters might still provide relatively acceptable resistance values and low permeability, these cells cannot provide applicable information with regard to the interaction of EVs with human brain endothelial cells. Rubin et al. introduced a BBB model based on culturing endothelial cells on a transwell® filter and treating the cells with cAMP and RO 20-1724, an inhibitor of cAMP degradation, with the aim of increasing intracellular cAMP levels [4]. This group has shown that an increase in the internal cAMP increases the expression of junctional features in brain endothelial cells and decreases the permeability of the barrier. While this model has not been used for EV-related studies, it provides the required properties for assessment of EV interactions with the BBB including their transcytosis. The model was optimized for this novel application. Human brain microvascular endothelial cells can be cultured on fibronectin-coated 0.4 um-pore filters ($25 \times 10^3$ cells per filter, 50 µg/ml fibronectin). The cells become confluent in 48-72 hours. At this time, 50 mM cAMP (8-CPT-cAMP) and 17 mM RO 20-1724 can be added to the media, as suggested [4]. The permeability of the barrier to different fluorescent tracers and the expression of tight junction molecules such as ZO-1 have been followed. The results show that 4 days after treatment with cAMP, the permeability of the barrier reaches an optimal state and the model can be subsequently used for assessment of transcytosis of EVs across the brain endothelial monolayer in vitro (FIGS. 1A to 1C).

Figure 2:
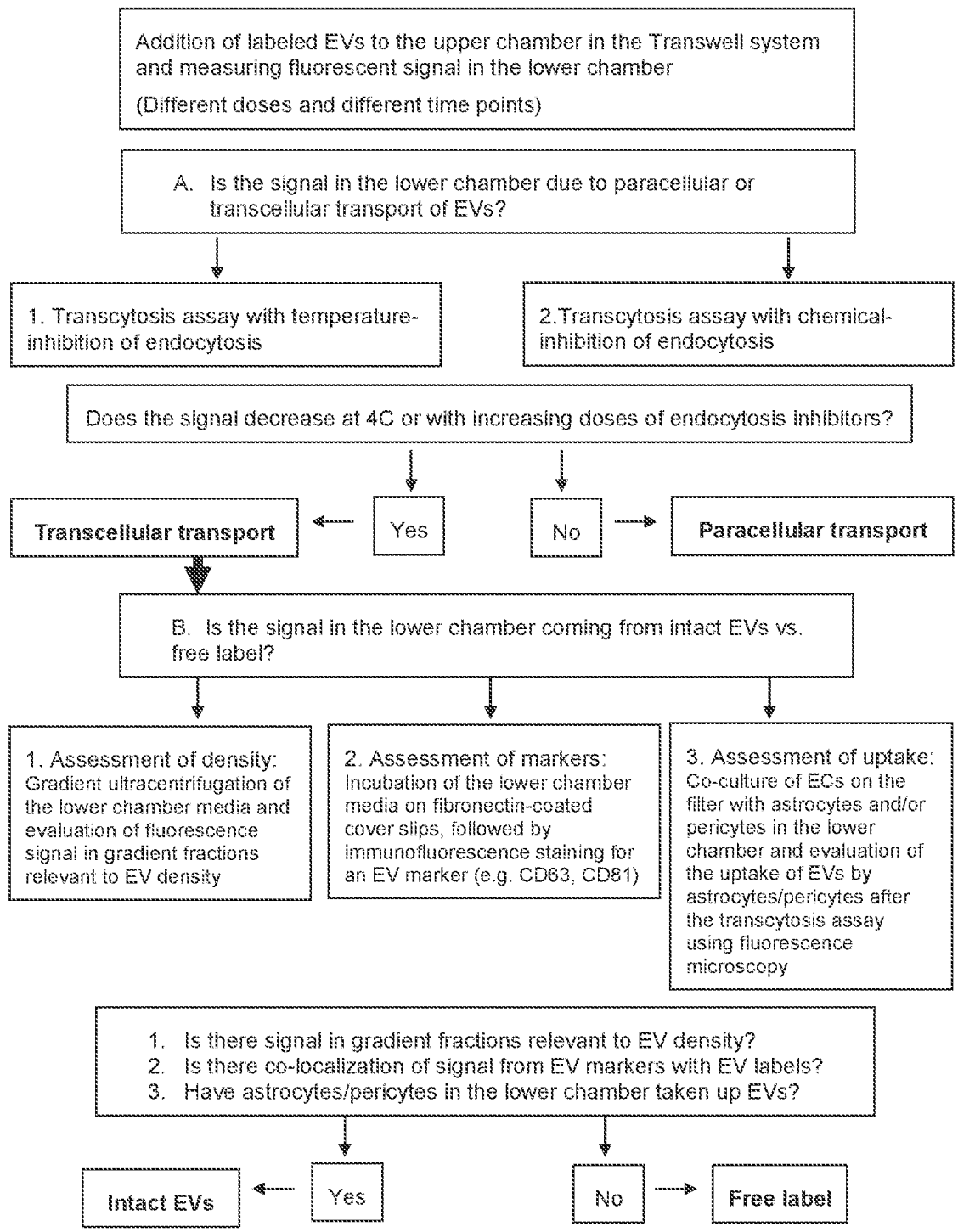
FIG. 2. Flowchart demonstrating a platform for in vitro assessment of the transcytosis of EVs across the BBB.

Description of the Platform for Assessment of EV Transcytosis through the BBB:

Traditionally, assessment of transcytosis of molecules using a transwell® model was made by fluorescent labeling or radiolabeling the molecule of interest and following the transport of the signal through the cells to the lower chamber of the transwell® model. Exploiting the abovementioned state-of-the-art labeling and the properties of the cAMP/RO 20-1724-treated transwell® model, the same concept can be used for assessment of the transcytosis of EVs across the BBB, in vitro. However, given the complexity of the structure of EVs, a series of approaches included in the platform is required to establish a reliable method of assessment. FIG. 2 demonstrates a flowchart describing the process of assessment of EV transcytosis in the platform.

Fluorescently labeled EVs can be added to the upper chamber in the transwell® model in different doses and the media from the lower chamber can be evaluated for fluorescence at different time points to assess the presence of a signal, dose-dependency as well as time-dependency of the signal intensity. These preliminary steps provide information regarding the likelihood of the presence of a transcellular transport process and can be used as a screening step when working with a variety of EVs (for therapeutic applications) to select for those with promising results to be included for the comprehensive assessment of transcytosis as follows:

Technical Details

Figure 3:
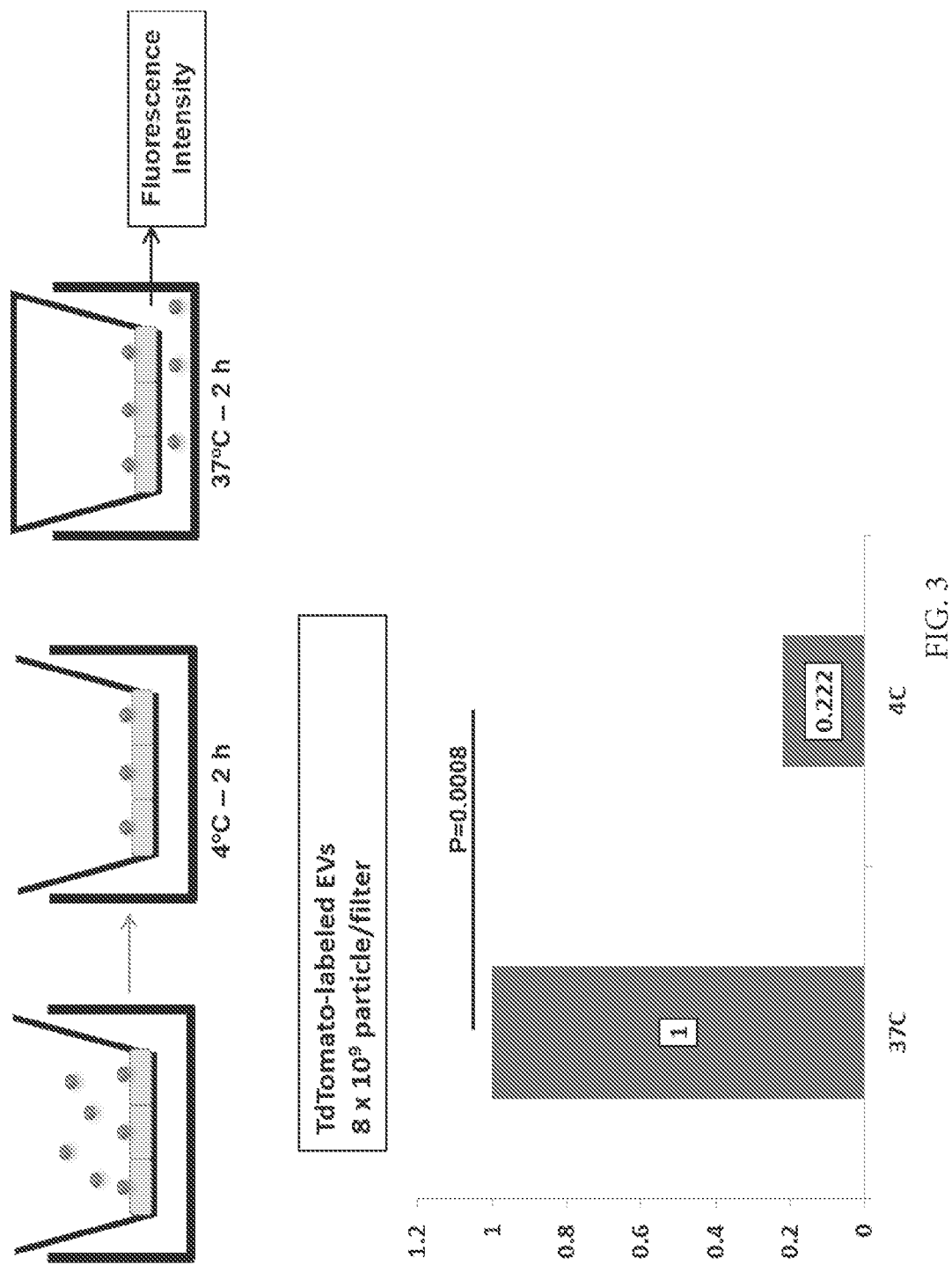
FIG. 3. Transcytosis assay with temperature-inhibition of endocytosis. Fluorescence intensity in the lower chamber is significantly lower at 4° C. compared to 37° C. This finding supports the transcellular transport of the fluorescent signal across the brain EC monolayer.

A. The first step to assess the transcytosis of EVs is to distinguish the transport of signal that is due to paracellular transport with that caused by transcellular transport. While the high integrity of the presented transwell® model supports the hypothesis that the presence of any signal in the lower chamber is most likely due to transcellular transport of the EVs, this should be further proven by two complementary approaches:

A-1) Transcytosis assay with temperature-inhibition of endocytosis: Transcytosis is an active process whereas paracellular transport occurs passively. As a result, transcytosis only occurs at 37° C. when the cells are active and will be stopped at low temperatures like 4° C. when the active mechanisms in the cell are halted. In contrast, paracellular transport can occur at both temperatures. A decrease in the intensity of the fluorescent signal in the lower chamber at 4° C. compared to 37° C. indicates that signal in the lower chamber can be due to transcellular transport of EVs (FIG. 3). The temperature-based approach is usually the only method used for assessment of transcytosis of different macromolecules. However, due to the larger size of EVs compared to most macromolecules and their vesicle structure, a decrease in temperature can potentially affect the Brownian movement of the EVs and affect the frequency of their binding to the cells. Accordingly, this approach should be complemented by a second chemical-based approach for more accuracy.

Figure 4:
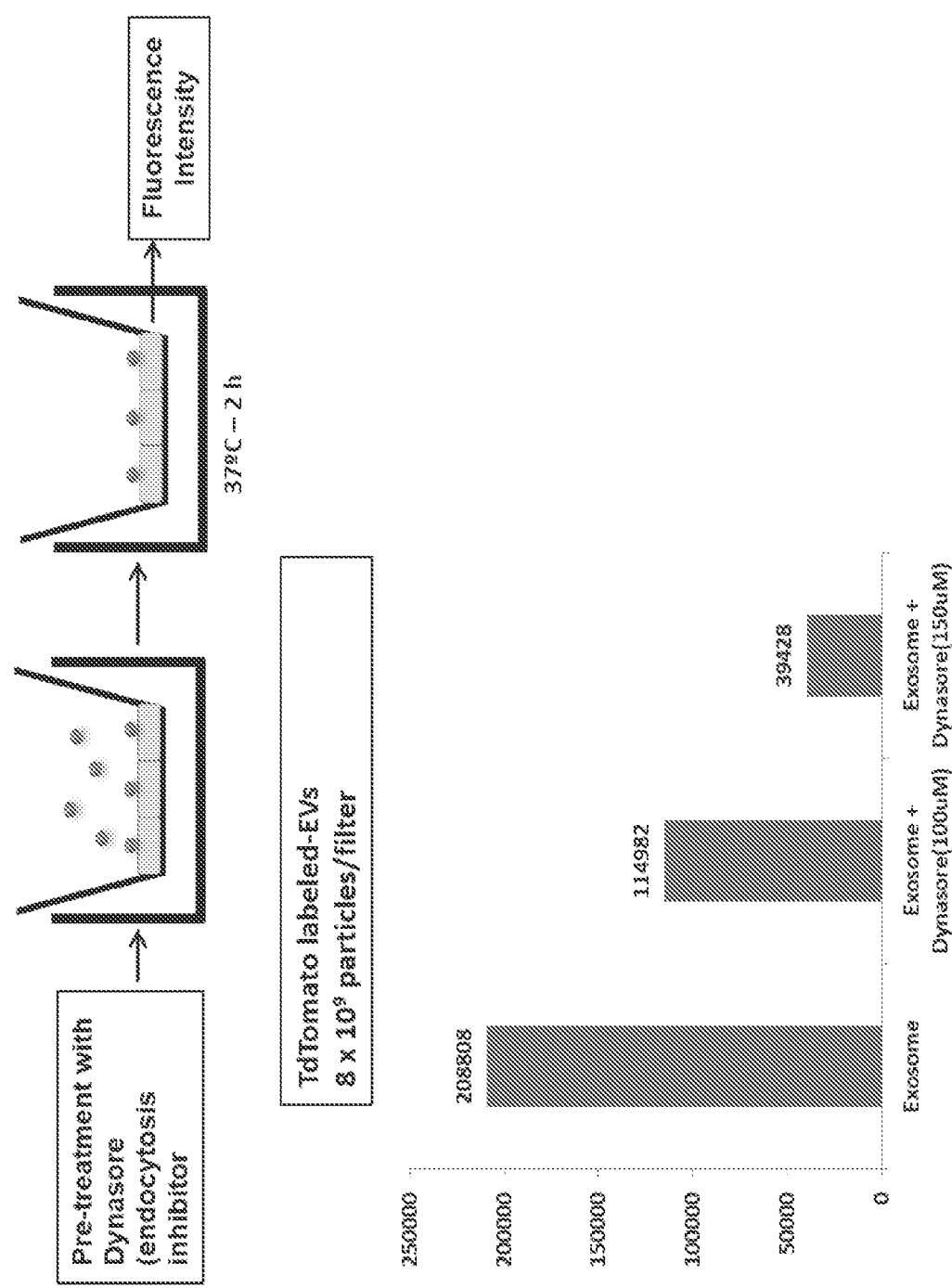
FIG. 4. Transcytosis assay with chemical-inhibition of endocytosis. Fluorescence intensity in the lower chamber is decreased with increasing doses of Dynasore, an inhibitor of endocytosis. This finding supports the transcellular transport of the fluorescent signal across the brain EC monolayer.

A-2) Transcytosis assay with chemical-inhibition of endocytosis: Transcytosis occurs following the uptake of macromolecules or EVs via endocytosis. Accordingly, inhibition of endocytosis will also inhibit transcytosis but it would not affect paracellular transport. A variety of chemicals that target different steps of endocytosis (e.g. Dynasore, filipin, etc.) can be used to pretreat the endothelial cells in the transwell® model to inhibit endocytosis prior to the transcytosis assay. A dose-dependent decrease in signal intensity in the lower chamber following the transcytosis assay is indicative of a transcellular transport (FIG. 4). It is worth to note that the endocytosis of EVs depends on the interaction of EV surface proteins with endothelial cell receptors, which depending on the EV proteins involved can go through different routes of endocytosis (clathrin-dependent, clathrin-independent, etc.). Therefore, using multiple types of inhibitors for endocytosis inhibition is suggested as well as complementing this approach with the temperature-inhibition method as explained above to accurately distinguish the route of EV transport.

Figure 5A:
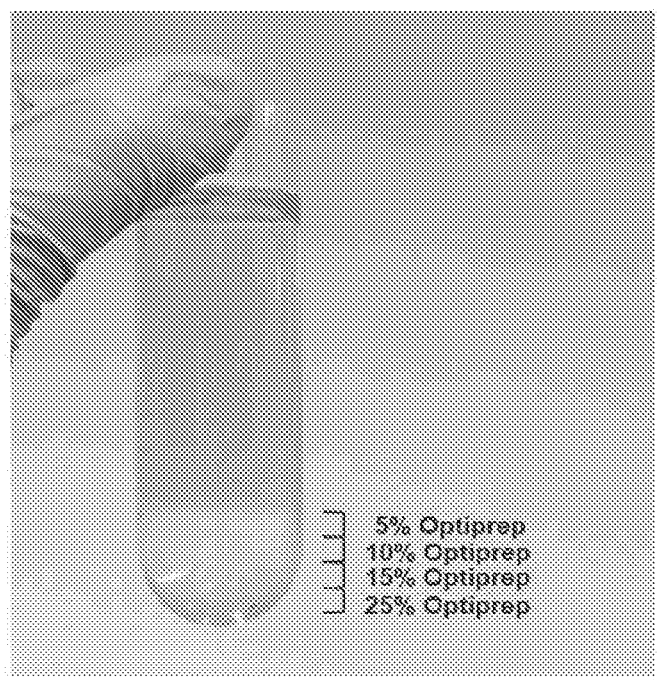
FIGS. 5A to 5C. Assessment of density.
Figure 5B:
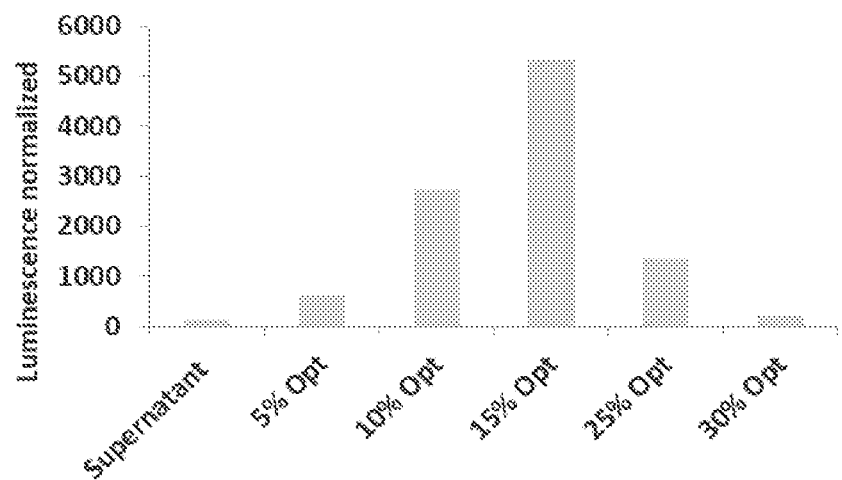
Figure 5C:
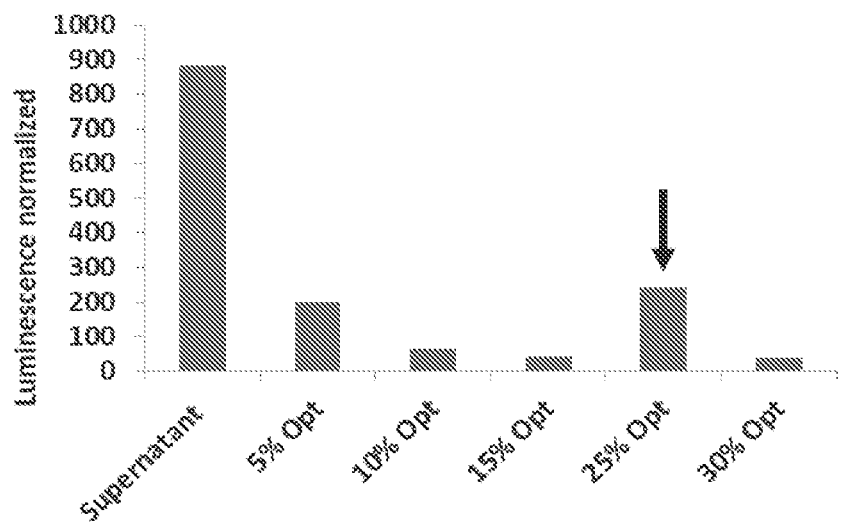

B. The second step in the presented platform for assessing the transcytosis of EVs is to determine the source of the fluorescent signal in the lower chamber of the transwell® model. Following the endocytosis of EVs, these complex vesicles can be processed by the cells which can release any sort of protein or chemical that has been used to label the EVs (membrane-bound or internal). Accordingly, for the assessment of the transcytosis, it is critical to determine that the fluorescent signal in the lower chamber analyzed in step A, is from intact EVs as oppose to free label/dye. To do so, a series of approaches were designed that analyze the characteristics of EVs in relation to the fluorescent signal. EVs are bilayered vesicles that have unique characteristics such as EV markers (e.g. CD63, CD9, etc.) and specific density and can be taken up by different cell types. These characteristics were used in the platform to distinguish between the fluorescent signal from intact EVs vs. free label:

B-1) Assessment of density: EVs have a density within a range of 1.09-1.2 $g/cm^3$ [2]. While this density might slightly differ within this range between the diverse types of EVs, it is significantly different to the density of free protein (1.4 $g/cm^3$). The density of EVs is generally determined by ultracentrifugation of EV-containing media on top of a sucrose or Iodixanol density gradient. The EVs will travel to a fraction with a density equal to theirs and the relevant fraction can be identified by analyzing the expression of EV markers in the different gradient fractions. In the platform, the same concept is used to assess the intactness of EVs in the lower chamber of the transwell® model. The media collected from the lower chamber can be ultracentrifuged on top of a density gradient. Following ultracentrifugation, each gradient fraction as well as the supernatant will be analyzed for fluorescence. Presence of fluorescent signal in any of the fractions relevant to EV density indicates that the source of the signal is intact EVs (FIGS. 5A to 5C). Free protein will remain on top of the gradient in the supernatant.

Figure 6:
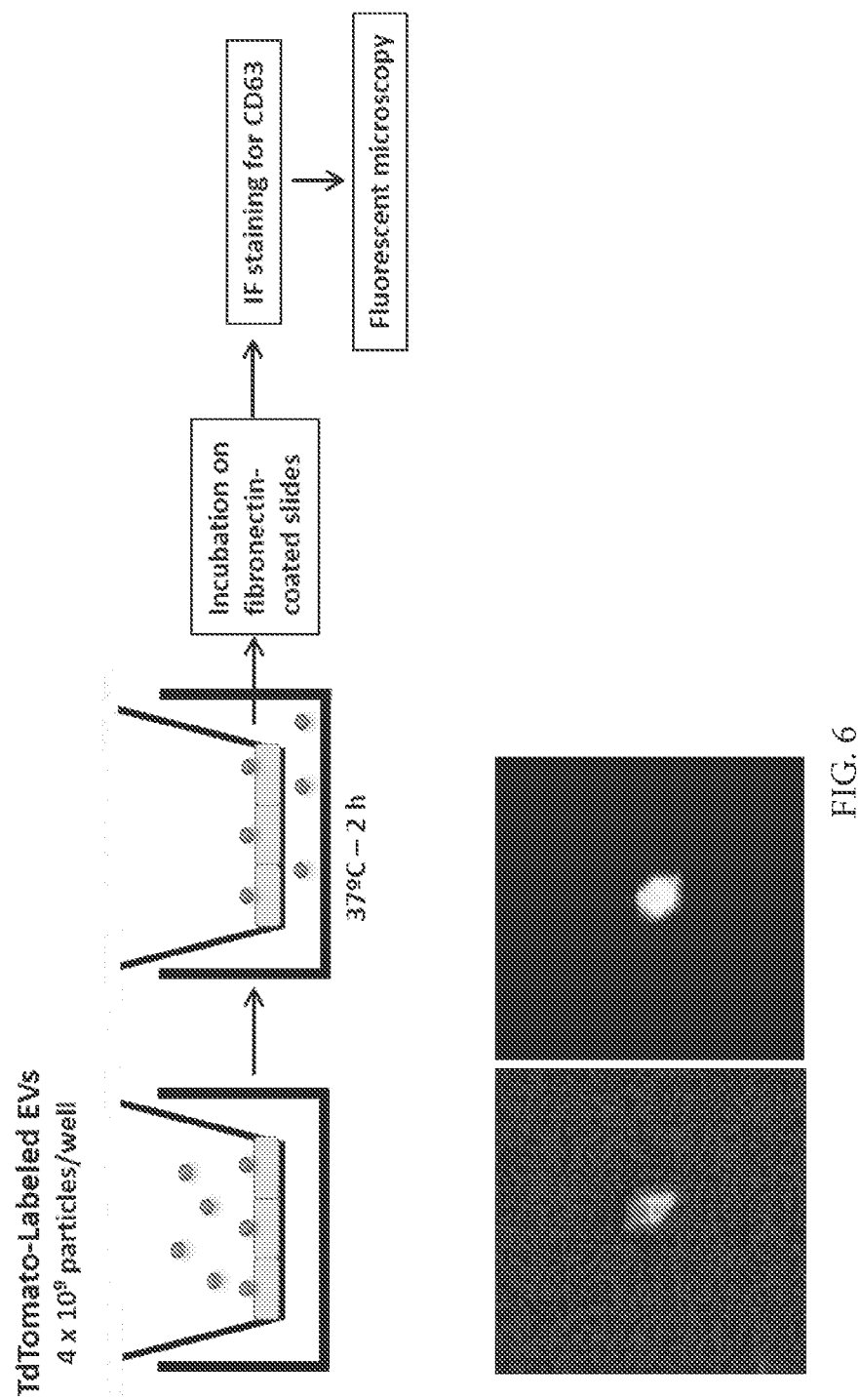
FIG. 6. Assessment of EV markers. The media collected from the lower chamber can be incubated on fibronectin-coated slides, following which immunofluorescence staining for different EV markers can be performed. A co-localization of red signal from TdTomato and green signal from the EV marker, CD63, demonstrates EVs as the source of the signal in the lower chamber.

B-2) Assessment of EV markers: EVs are characterized by a variety of markers including certain tetraspanins such as CD63, CD81, and CD9 [2]. To determine the source of fluorescent signal in the lower chamber in the transcytosis assay, co-localization of the fluorescent signal from the EV label with any of these markers indicates EVs as the source of the fluorescent signal, supporting the transcytosis of EVs. For this purpose, the following approach was incorporated in the platform: The media collected from the lower chamber in a transcytosis assay can be incubated on fibronectin-coated cover slips for 1-2 hours. It has been shown that EVs tend to attach to fibronectin; however, any type of extracellular matrix molecule can be used for this purpose, if their attachment to EVs has been determined in advance. Following this incubation, the cover slips can be fixed and stained by immunofluorescent technique using an antibody against one or more of the EV markers. Co-localization of the fluorescent signal from the EV label and the fluorescent signal from the EV markers can be evaluated by fluorescent microscopy (FIG. 6).

Figure 7:
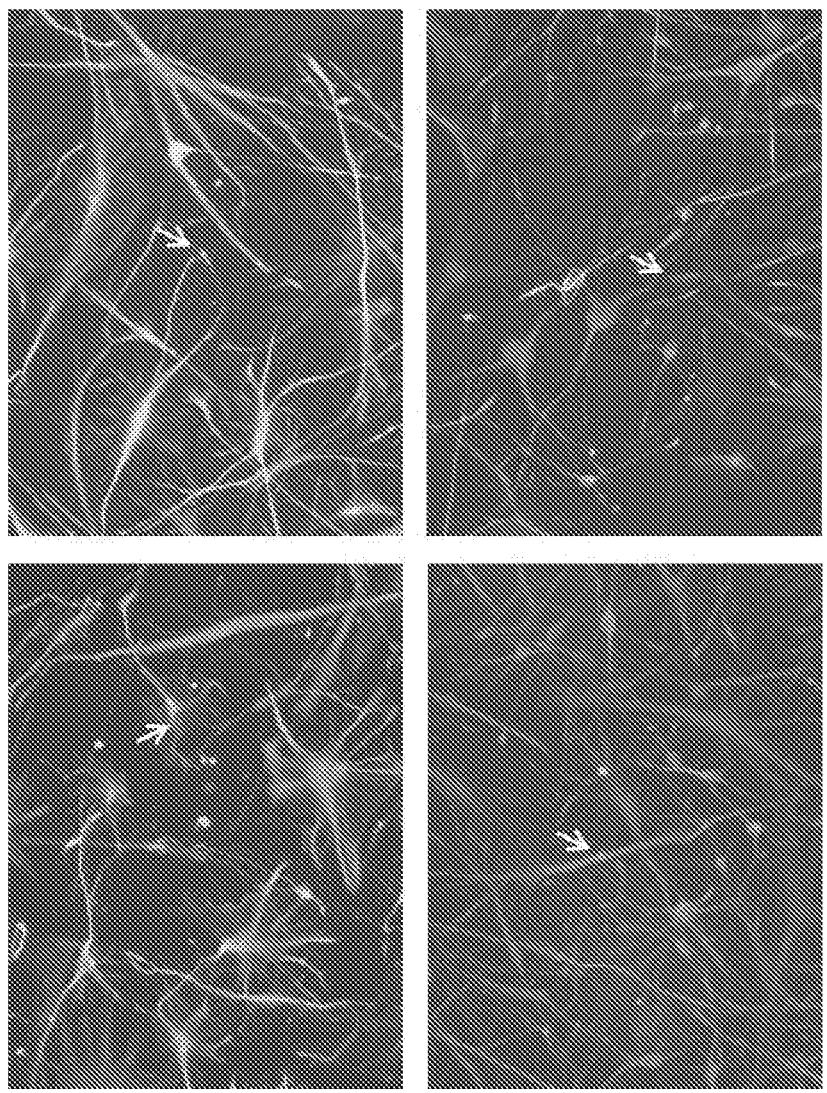
FIG. 7. Assessment of EV uptake by astrocytes. Astrocytes can be co-cultured with brain ECs in the lower chamber of the transwell® model. Uptake of EVs by astrocytes (white arrows) following the transcytosis assay supports EVs as the source of fluorescent signal in the lower chamber.

B-3) Assessment of EV uptake: EVs can be taken up by a variety of cells mostly through endocytosis in contrast to fusion uptake that is mostly seen for liposomes and free membrane dyes [2]. This uptake can be evaluated by co-culturing astrocytes and/or pericytes, the other two components of the BBB, with the brain endothelial cells in the presented transwell® model. Astrocytes and pericytes can be cultured on cover slips in the lower chamber. Following preparation of the model and the transcytosis assay, the cover slips can be stained with astrocyte and/or pericyte markers and to evaluate EV uptake. Presence of fluorescent dots inside the cells mostly indicates that EVs are the source of the fluorescence signal in the lower chamber (FIG. 7), whereas fluorescent signal from free label will mostly be seen at the cell membrane as the label incorporates into the cell membrane.

Figure 8A:
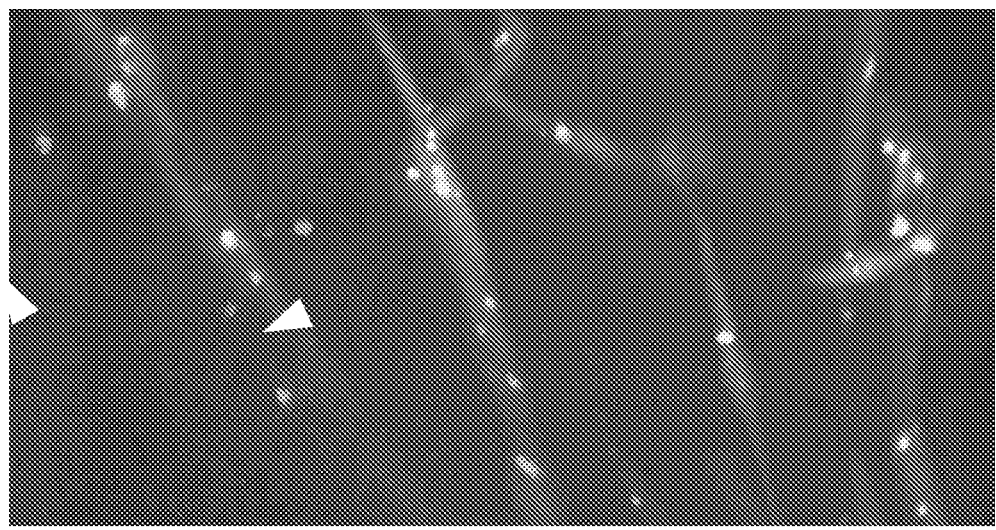
FIGS. 8A to 8B. Exosomes can cross the BBB in a zebrafish model.
Figure 8B:
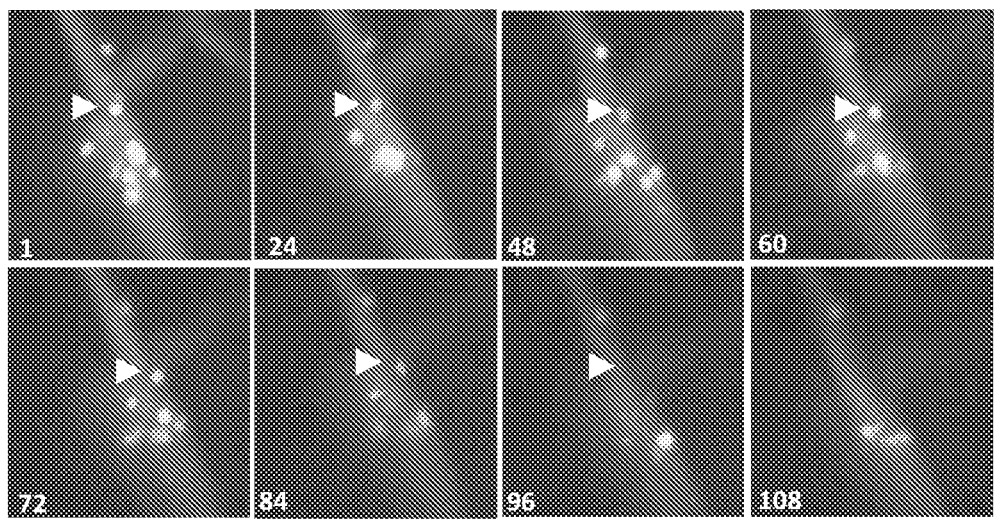
Figure 9:
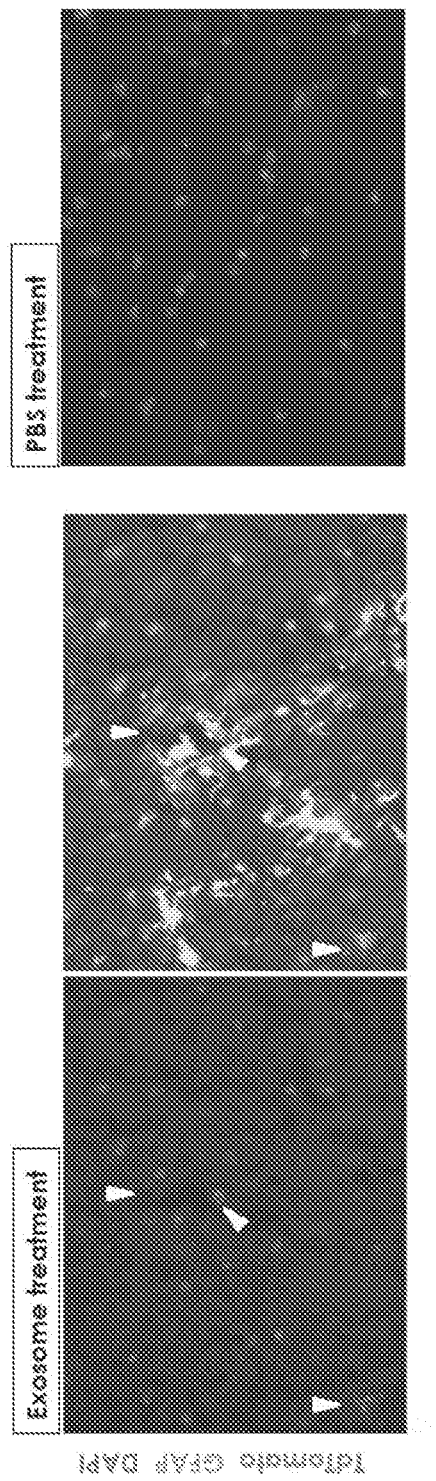
FIG. 9. Exosomes can be taken up by astrocytes in vivo. TdTomato 231Br-Ex are taken up by astrocytes after the retro-orbital injection of exosomes. No signal was detected in the control animal treated with PBS.
Figure 10A:
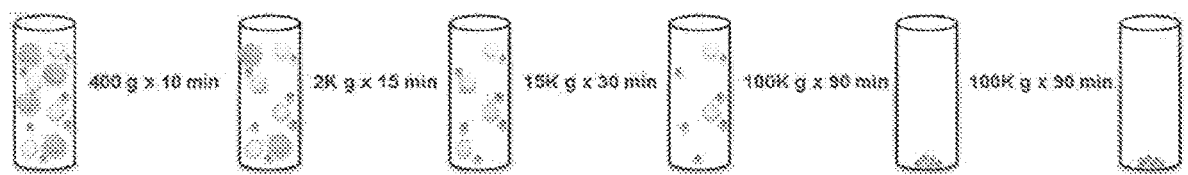
FIGS. 10A-10D. Exosome isolation and characterization.
Figure 10B:
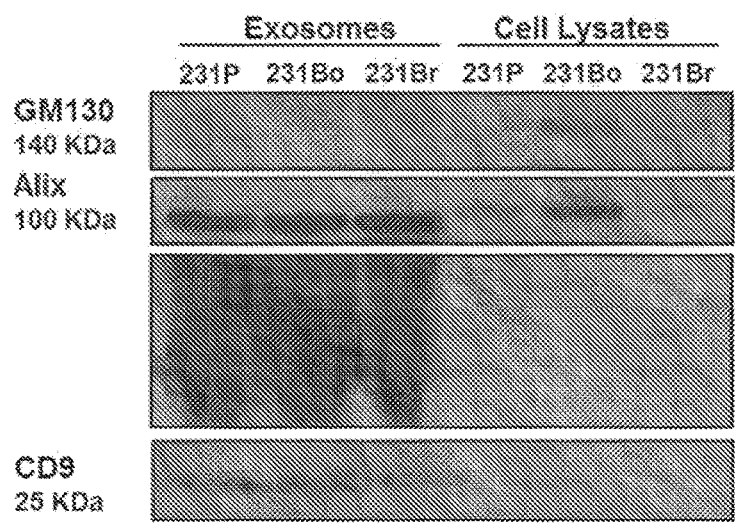
Figure 10C:
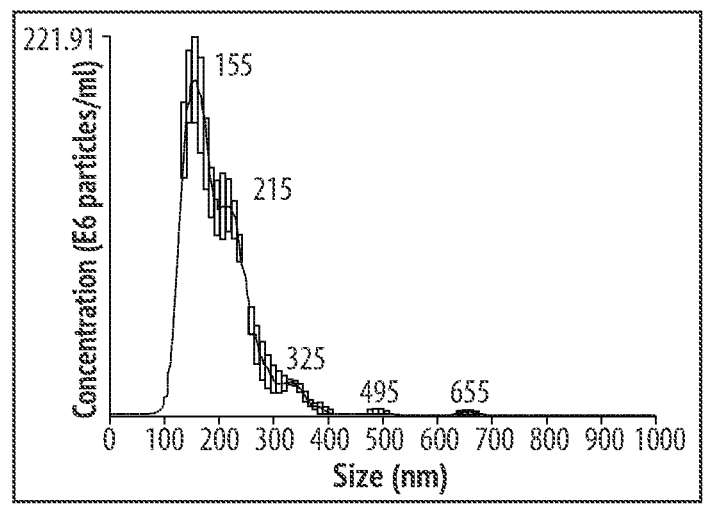
Figure 10C:
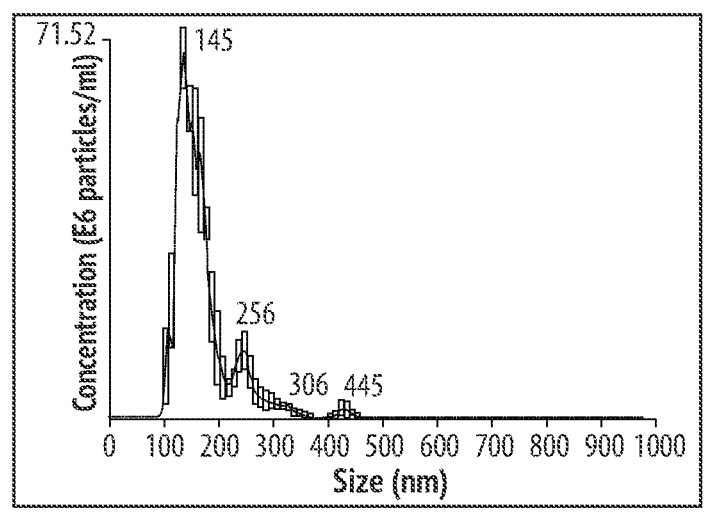
Figure 10C:
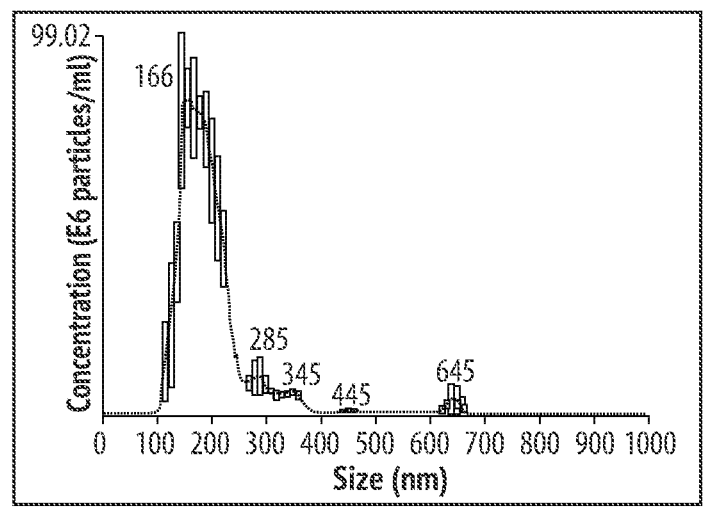
Figure 10D:
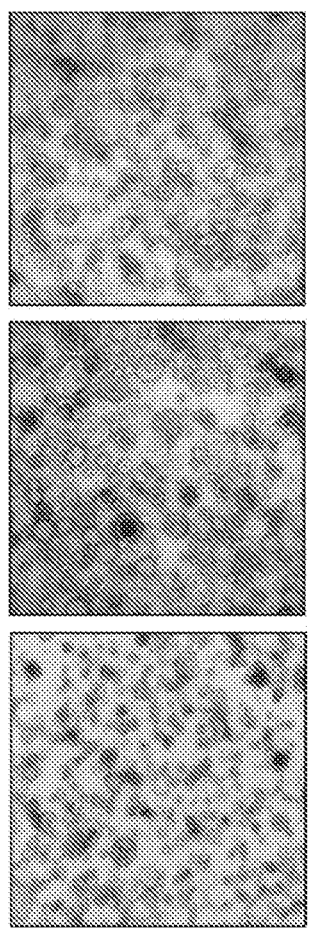

Using live imaging and histological evaluations in zebrafish (FIGS. 8A to 8B) and mouse models (FIG. 9), the validity of the abovementioned findings has further been confirmed with regard to the transcytosis of EVs across the brain endothelium. This consistency between the in vitro and in vivo findings demonstrates the high reliability of the presented platform for assessment of the transcytosis of EVs across the BBB as an early tool that could facilitate the bench-to-bedside translation of EVs as potential diagnostics and therapeutics.

Example 2

Using Proteomics Profiling to Elucidate the Interactions of Breast Cancer-Derived Exosomes with the Blood Brain Barrier The development of brain metastasis is associated with a significant reduction in the survival rate of breast cancer patients. Improving the prognosis of women with brain metastasis from breast cancer relies on the elucidation of the mechanisms underlying this process. It has been shown that the formation of brain metastases occurs along the abluminal side of brain vessels, a process called "vessel co-option". These observations prompted the hypothesis that the cellular and extracellular matrix (ECM) components of the blood-brain-barrier (BBB) can serve as a pre-metastatic niche for breast cancer brain metastases. The role of tumor-derived exosomes (TEx) in the preparation of a pre-metastatic niche in distant organs has been shown in a number of cancers.

To investigate the mechanisms driving the vessel co-option of breast cancer brain metastases, the role of breast cancer-derived exosomes in preparation of the BBB for metastasis formation was studied. Exosomes were isolated from the MDA-MB-231 breast cancer cell line, a brain-seeking variant of these cells, and a bone-seeking variant as a non-brain metastatic control. Brain endothelial cells, astrocytes, and brain vascular pericytes, the three components of the BBB, were treated with exosomes for 3 days to recapitulate the continuous exposure of cells to the circulating TEx in vivo. The treated cells were analyzed for cellular activities relevant to pre-metastatic niche preparation in the brain such as the integrity of the BBB, expression of cytokines, and modulation of the ECM. An initial screen was performed using cytokine antibody arrays and PCR arrays for ECM and adhesion molecules and results were validated in three separate experiments using western blots, ELISA, and Multiplex assays.

Exosomes derived from brain-seeking cells significantly increased astrocyte migration and decreased the expression of Integrin β1 in brain endothelial cells, both of which can lead to the disruption of the BBB integrity. Moreover, the expression of Interleukin 8 was increased by TEx in astrocytes. TEx also increased the expression of MMP-3 and -9 (Matrix Metalloproteinases) from an undetectable baseline level and decreased the expression of TIMP-1 and -2 (Tissue Inhibitors of MMPs) in astrocytes. While the importance of these two MMPs for brain metastasis from breast cancer has been previously reported, this study is the first to demonstrate that secretion of these MMPs is triggered by TEx. No significant TEx-derived modulations in the expression of cytokines, ECM, and adhesion molecules in brain pericytes were observed.

Figure 11:
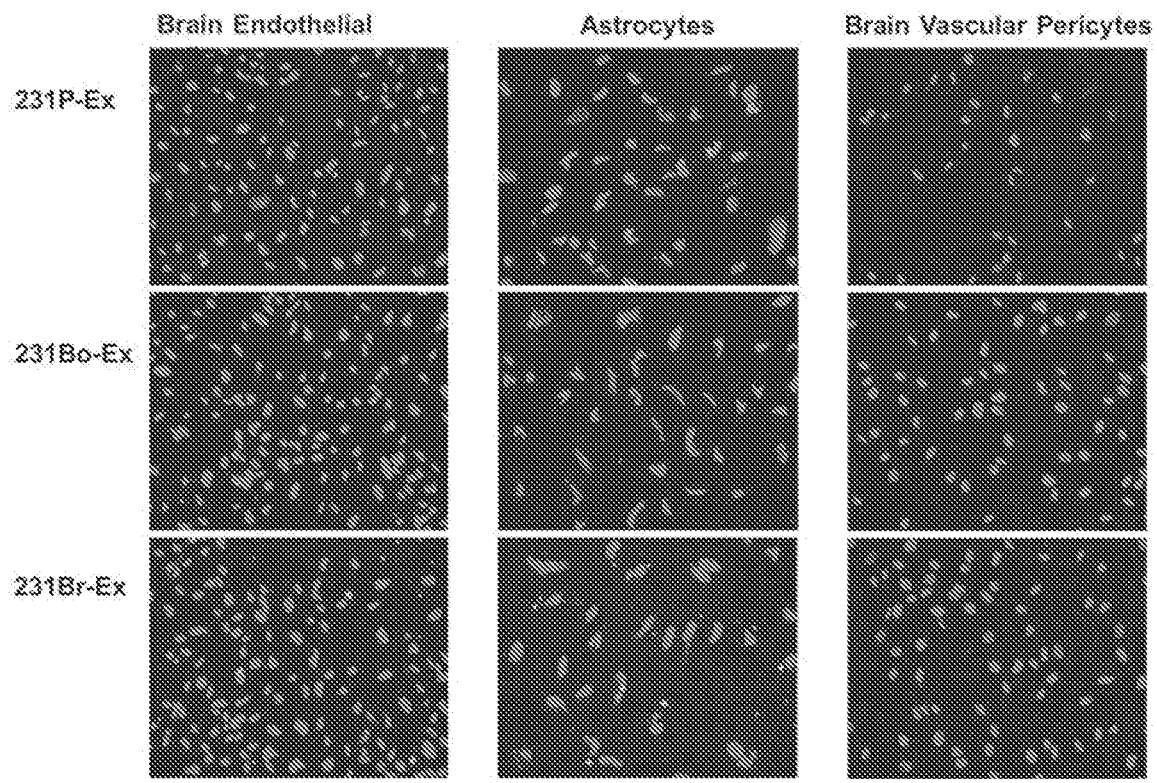
FIG. 11. Uptake of exosomes by brain endothelial cells, astrocytes, and pericytes. TdTomato labeled exosomes were incubated with cells for 2 hours and visualized.
Figure 12A:
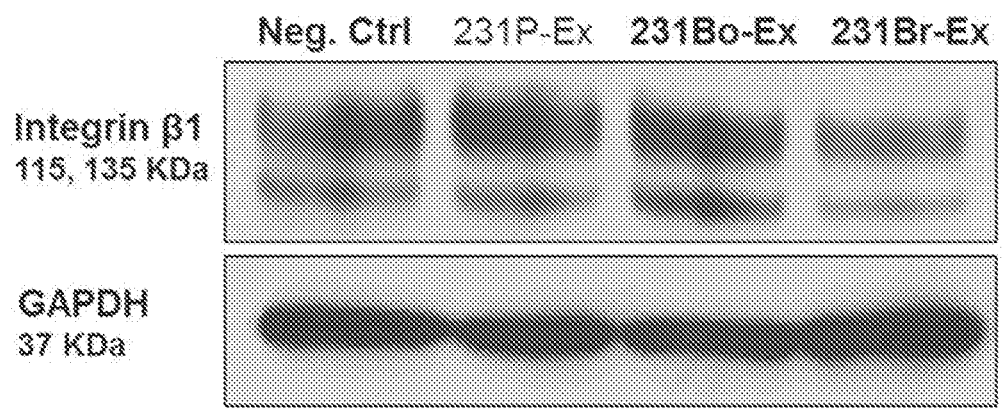
FIGS. 12A to 12B. The effect of exosomes on brain endothelial cells. Continuous treatment of brain microvascular endothelial cells with 5 µg/ml tumor-derived exosomes for 3 days resulted in a significant decrease in expression of integrin β1 shown by western blot (FIG. 12A), and flow cytometry (FIG. 12B).
Figure 12B:
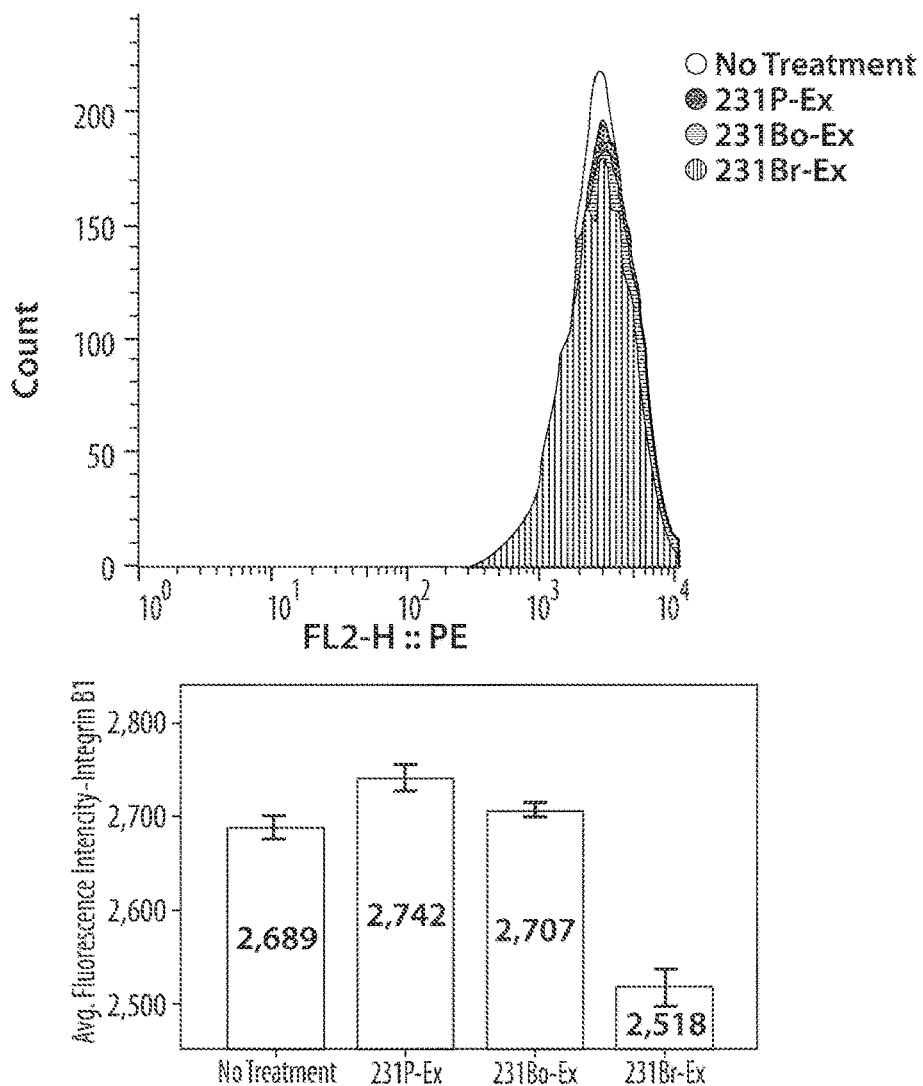
Figure 13:
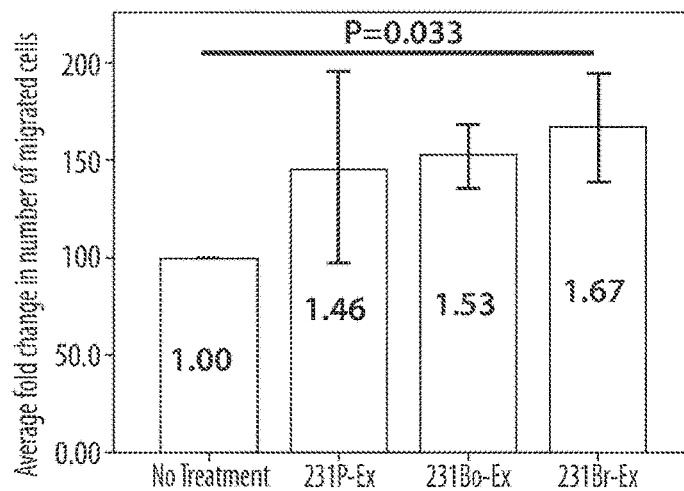
FIG. 13. The effect of exosomes on the migration of astrocytes. Continuous treatment with exosomes derived from MDA-MB-231 brain seeking cells (5 µg/ml for 3 days) resulted in a significant increase in cell migration in a Transwell® assay. Data from four separate experiments, run in duplicates.
Figure 14:
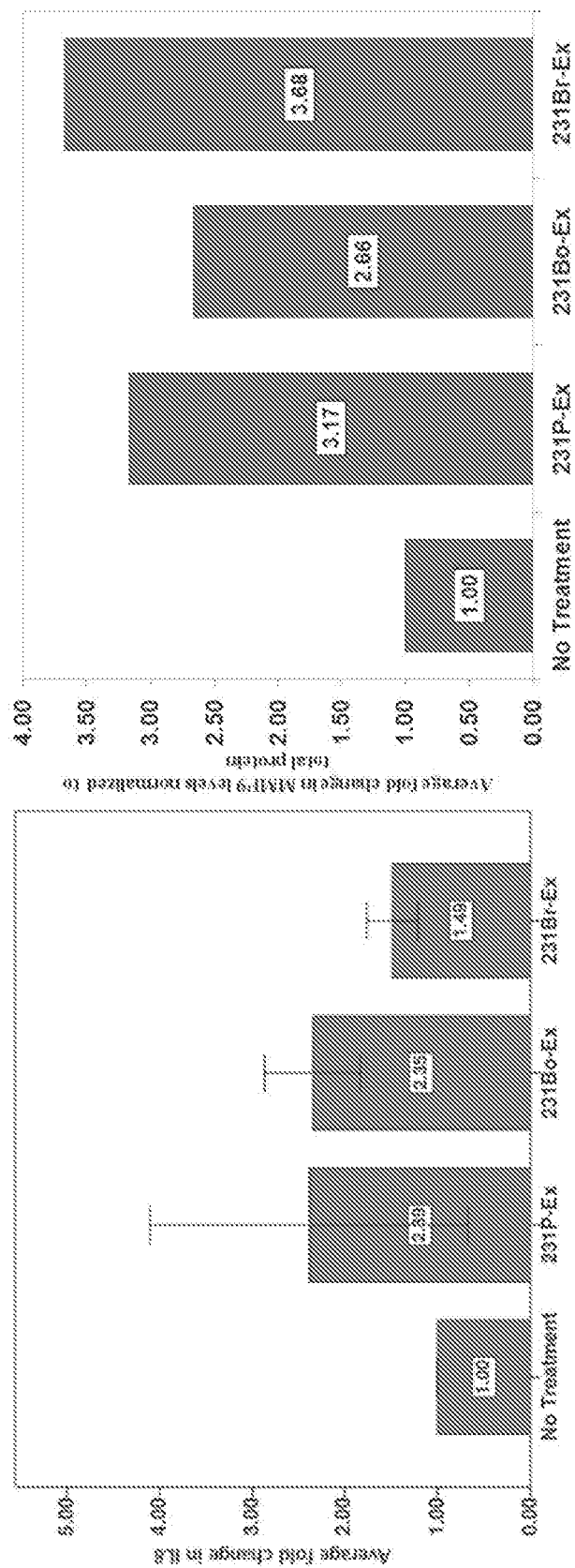
FIG. 14. The effect of exosomes on the protein expression profile of astrocytes. Continuous treatment with MDA-MB-231-derived exosomes (5 µg/ml for 3 days) increased the expression of IL-8 and MMP9 in astrocytes shown by ELISA. IL-8 data from three separate experiments, run in duplicates.
Figure 15:
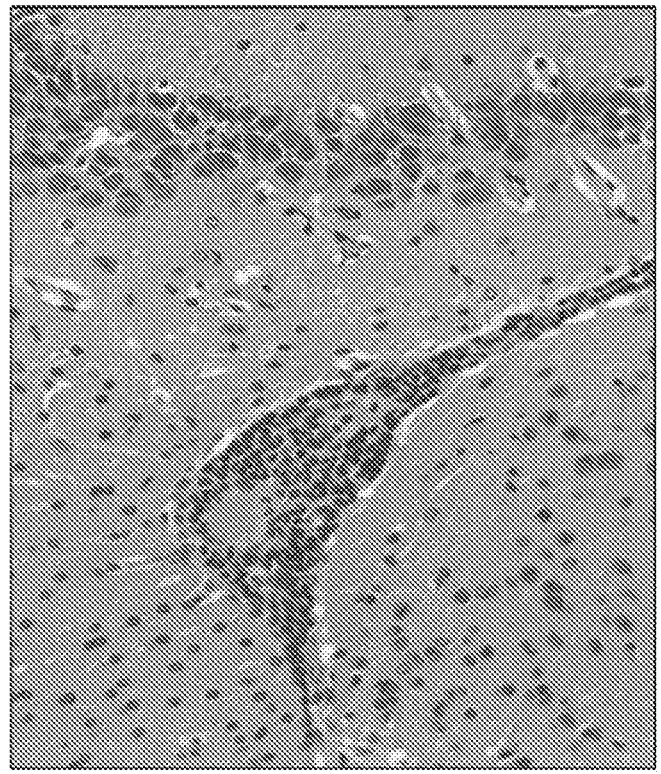
FIG. 15. MMP9 overexpression in vivo. Nude mice received intracardiac injection of MDA-MB-231 brain-seeking cells to induce brain metastasis. Micrometastases formed around the vessels (H&E staining, right panel). IHC staining for MMP9 showed overexpression of MMP9 around the vessels at the site of micrometastases as compared to normal vasculature in brain (left panel).
Figure 15:
Figure 16:
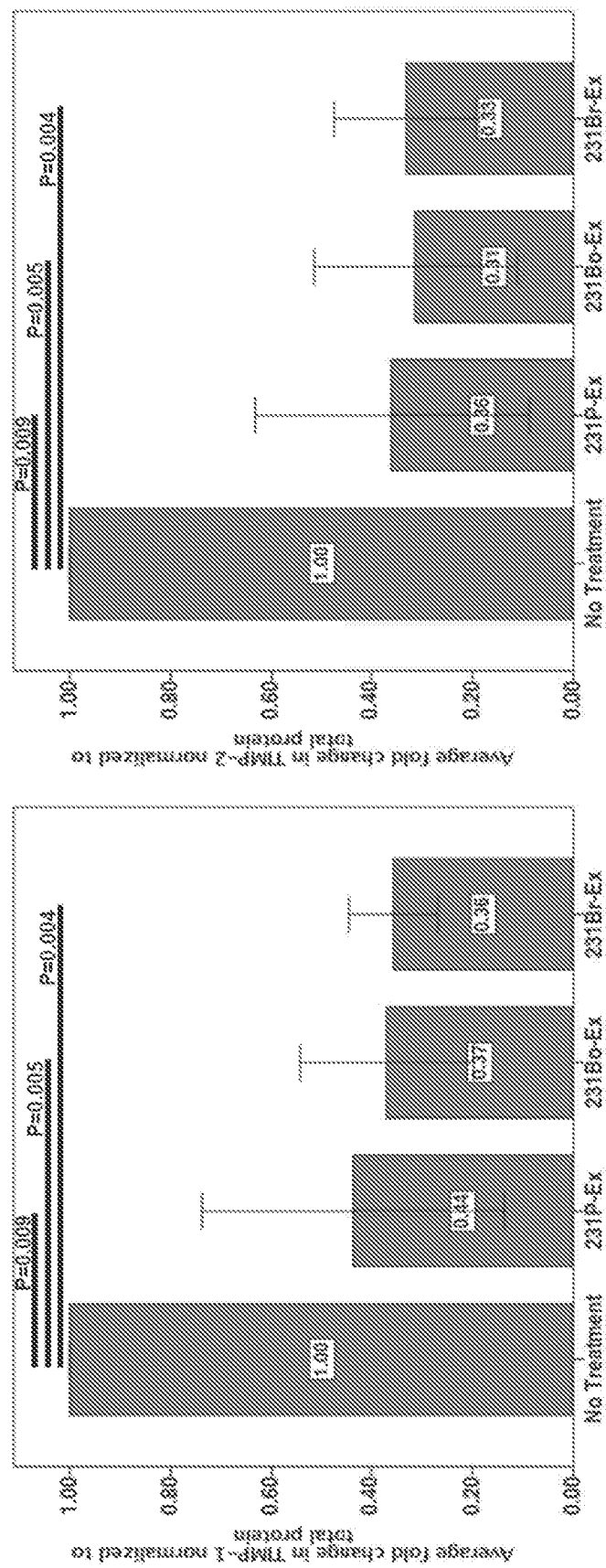
FIG. 16. Incubation of astrocytes with MDA-MB-231-derived exosomes (50 µg/ml for 48 h) significantly decreased the expression of TIMP-1 and TIMP-2, shown by ELISA. Data from three separate experiments, run in duplicates.

These findings indicate that within the BBB, astrocytes and endothelial cells, but not pericytes, can be affected by breast cancer-derived exosomes in such a way that can potentially lead to preparation of a suitable niche for future metastasis formation along the brain vasculature. For example, the findings show that brain endothelial cells and astrocytes can uptake parental and brain-seeking MDA-MB-231-derived exosomes, while brain vascular pericytes do not uptake the MDA-MB-231-derived exosomes (FIG. 11). Further, exosomes derived from MDA-MB-231 brain-seeking cells significantly decreased the surface expression of Integrin β1 on brain microvascular endothelial cells (FIGS. 12A and 12B) and significantly increased the migration of astrocytes (FIG. 13). It was also observed herein that exosomes derived from MDA-MB-231 parental, bone-, and brain-seeking cells increased the expression of MMP9 in astrocytes (FIG. 15), significantly decreased the expression of TIMP-1 and TIMP-2 in astrocytes (FIG. 16), but did not induce any alteration in the expression of cytokines, extracellular matrix proteins, and adhesion molecules in brain vascular pericytes (FIG. 14). Metastasis of MDA-MB-231 brain-seeking cells to brain in mice was associated with an overexpression of MMP-9 around the vasculature harboring the micrometastases.

Figure 17:
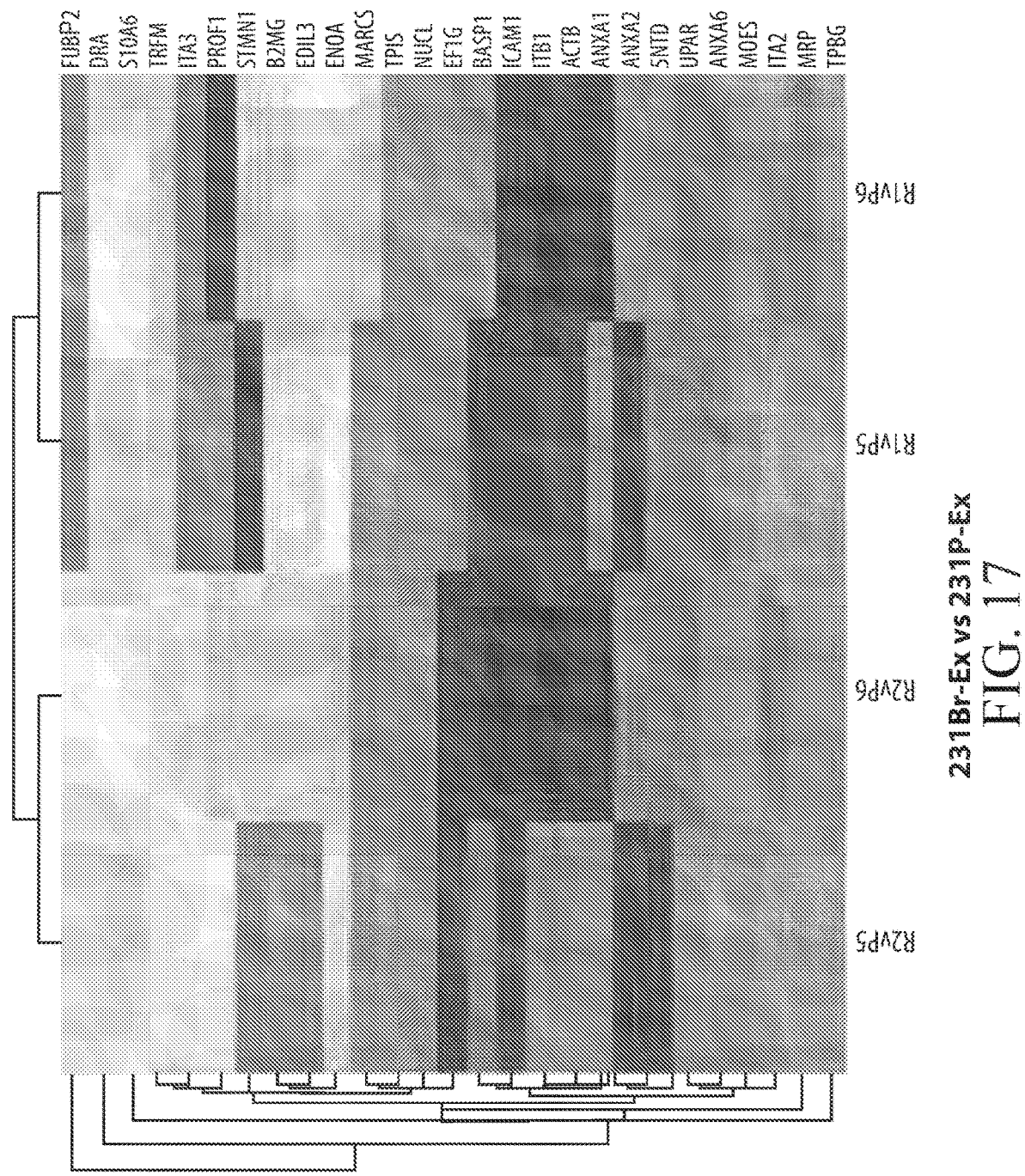
FIG. 17. Quantitative proteomics demonstrates a number of proteins enriched in the brain-seeking exosomes compared to the parental and the bone-seeking exosomes.
Figure 17:
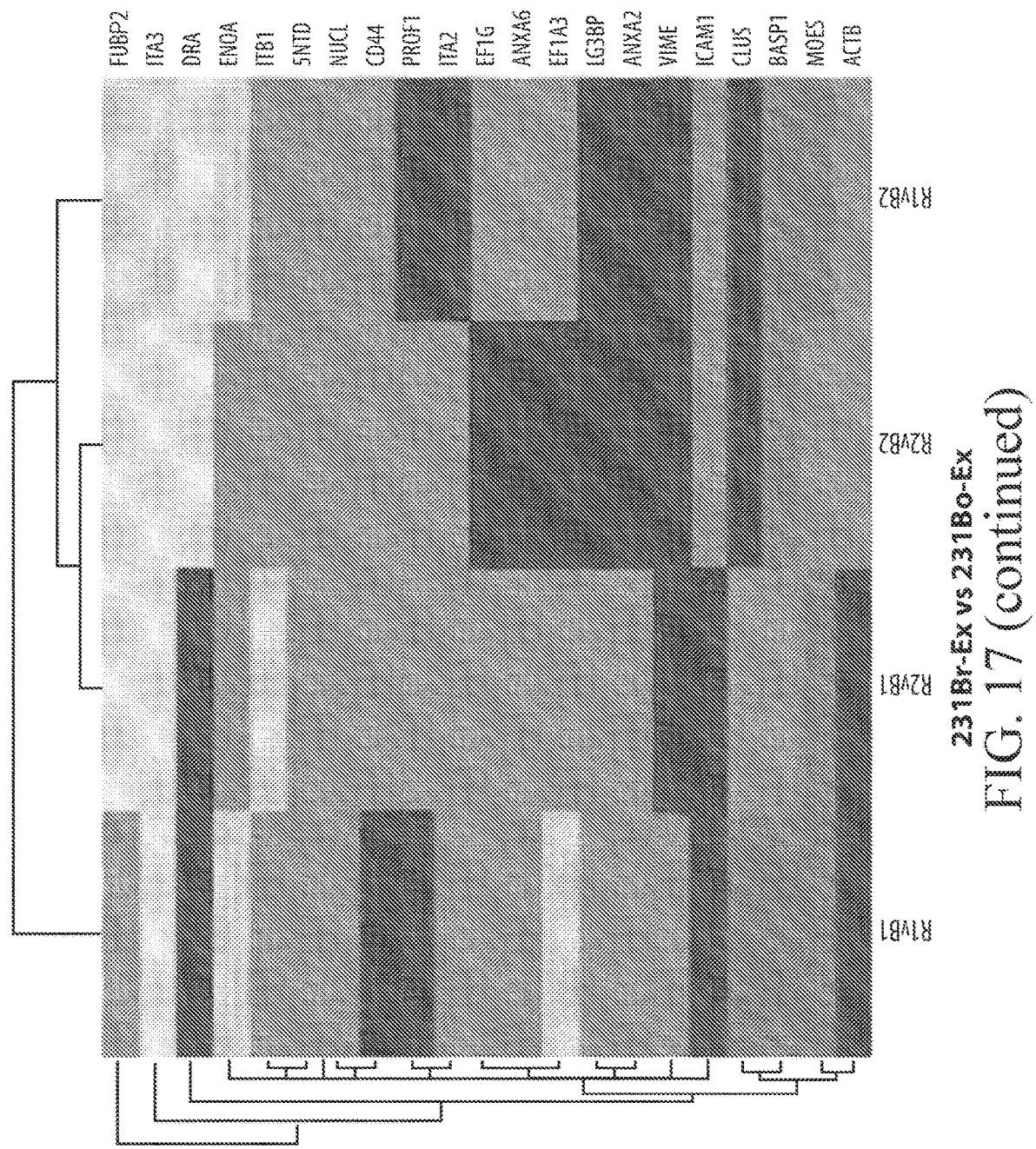

Elucidation of the early events leading to brain metastasis is essential to the development of more effective therapeutic and diagnostic approaches. Exosomes derived from a brain-seeking variant of the breast cancer cell line MDA-MB-231 (Br-Ex) can facilitate brain metastasis by inducing alterations in the protein expression profile of astrocytes, one of the components of the blood brain barrier (BBB). It was hypothesized that the interaction(s) between exosomes and astrocytes is more efficient compared to brain endothelial cells (ECs) or pericytes, the two additional major components of the BBB, resulting in more prominent alterations in the protein expression profile of astrocytes. To test this hypothesis, the uptake of exosomes by brain ECs, astrocytes, and pericytes in vitro was quantified and compared. The uptake of Br-Ex by astrocytes was significantly greater than that of brain ECs ($P<4e-3$) and pericytes ($P<1e-3$). In contrast, exosomes derived from parental or bone-seeking MDA-MB-231 cells (P-Ex and Bo-Ex, respectively) did not show a preferential uptake by astrocytes. The uptake of Br-Ex by astrocytes in vivo was also demonstrated. The uptake of exosomes by different cell types predominantly relies on the interaction of exosomal proteins with different receptors on the recipient cells. To determine the exosomal proteins potentially involved in the preferential uptake of Br-Ex by astrocytes, quantitative mass spectrometry was performed on the P-, Bo-, and Br-Ex via Isobaric Tag for Relative and Absolute Quantitation (iTRAQ) analysis. Database searches were performed against human proteins in the SwissProt database and a total of 126 proteins were detected with over 95% confidence. Pairwise comparisons identified a total of 27 and 21 proteins with statistically significant differential expression ($P<0.05$) in the Br-Ex compared to the P- and Bo-Ex, respectively (FIG. 17). Functional enrichment analysis of the detected proteins demonstrated that proteins belonging to the cell migration and focal adhesion categories were over-represented in the Br-Ex. Among these proteins, a number of integrins and annexins were highly enriched in the Br-Ex and can potentially be involved in the preferential uptake of these exosomes by astrocytes.

These findings indicate that exosomes derived from brain-seeking breast cancer cells can preferentially interact with astrocytes and these interactions can be driven by exosomal integrins and annexins.

REFERENCES

Abbott, N. J., *Blood-brain barrier structure and function and the challenges for CNS drug delivery*. J Inherit Metab Dis, 2013. 36(3): p. 437-49.
Abels, E. R. and X. O. Breakefield, *Introduction to Extracellular Vesicles: Biogenesis, RNA Cargo Selection, Content, Release, and Uptake*. Cell Mol Neurobiol, 2016. 36(3): p. 301-12.
Lai, C. P., et al., *Visualization and tracking of tumour extracellular vesicle delivery and RNA translation using multiplexed reporters*. Nat Commun, 2015. 6: p. 7029.
Rubin, L. L., et al., *A cell culture model of the blood-brain barrier*. J Cell Biol, 1991. 115(6): p. 1725-35.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of quantifying transcytosis of an extracellular vesicle (EV) across the blood brain barrier (BBB), the method comprising:
    (i) contacting the EV with a layer of brain endothelial cells cultured on a permeable cell culture insert that divides a cell culture well into an upper chamber and a lower chamber, wherein the contacting of the EV with the layer of brain endothelial cells occurs in one of the upper chamber and the lower chamber, and wherein the brain endothelial cells are treated with an agent that increases intracellular cyclic AMP (CAMP) level;
    (ii) detecting an EV signal in the other one of the upper chamber and the lower chamber; and (iii) quantifying the EV signal detected in (ii) from EVs that crossed the layer of brain endothelial cells via transcytosis, wherein the EV signal is higher than a control signal.

2. The method of claim 1, wherein the EV is added to the upper chamber and the EV signal is detected in the lower chamber.

3. The method of claim 1, wherein the EV is added to the lower chamber and the EV signal is detected in the lower chamber.

4. The method of claim 1, wherein the EV is labeled with a fluorescent molecule or a radioisotope.

5. The method of claim 1, wherein the control EV signal is obtained by performing steps (i)-(iii) at a low temperature that inhibits endocytosis.

6. The method of claim 1, further comprising:
(iv) determining the EV signal detected in step (ii) is from an intact EV.

7. The method of claim 6, wherein step (iv) comprises detecting the colocalization of EV signal and an EV biomarker.

8. The method of claim 7, wherein the EV biomarker is selected from the group consisting of: CD63, CD9, CD81, Alix, TSG101, Flotillin, Annexins, Integrins.

9. The method of claim 1, wherein the agent that increases intracellular cAMP level is cAMP or an inhibitor of cAMP degradation.

10. The method of claim 1, wherein the EV is an exosome, microvesicle, microparticle, ectosome, oncosome, or apoptotic body.

11. The method of claim 1, wherein the EV is isolated from a cancer cell or is an engineered EV.

12. The method of claim 11, wherein the engineered EV encapsulates a drug for the brain.

13. A method of determining the likelihood of brain metastasis of a cancer cell, the method comprising quantifying transcytosis of an extracellular vesicle (EV) isolated from the cancer cell across the blood brain barrier (BBB) using the method of claim 1, wherein the cancer cell is determined to have high likelihood of brain metastasis when the EV signal is higher than the control signal.

14. The method of claim 13, wherein the cancer is selected from the group consisting of: breast cancer, lung cancer, melanoma, colorectal cancer, and pancreatic cancers.

15. The method of claim 13, wherein the cancer cell is isolated from a subject.

16. The method of claim 15, further comprising treating the subject to reduce the likelihood of brain metastasis if the EV isolated from the cancer cell can cross the BBB.

17. The method of claim 1, wherein the control EV signal is obtained by treating the brain endothelial cells of step (i) with an agent that inhibits endocytosis prior to performing steps (ii) and (iii).

18. A method of quantifying transcytosis of an extracellular vesicle (EV) across an endothelial barrier, the method comprising:
(i) contacting the EV with a layer of endothelial cells cultured on a permeable cell culture insert that divides a cell culture well into an upper chamber and a lower chamber, wherein the contacting of the EV with the layer of endothelial cells occurs in one of the upper chamber and the lower chamber, and wherein the brain endothelial cells are treated with an agent that increases intracellular cyclic AMP (cAMP) level;
(ii) detecting an EV signal in the other one of the upper chamber and the lower chamber; and
(iii) quantifying the EV signal detected in (ii) from EVs that crossed the layer of endothelial cells via transcytosis, wherein the EV signal is higher than a control.

19. The method of claim 18, wherein the endothelial cells are brain endothelial cells, lung endothelial cells, gastrointestinal endothelial cells, bone marrow endothelial cells, or renal endothelial cells.

20. The method of claim 19, wherein the endothelial cells are bone marrow endothelial cells.

21. The method of claim 20, wherein the bone marrow endothelial cells are treated with an inflammatory cytokine.

* * * * *

UNITED STATES PATENT AND TRADEMARK OFFICE
CERTIFICATE OF CORRECTION

PATENT NO. : 12,241,888 B2
APPLICATION NO. : 16/979710
DATED : March 4, 2025
INVENTOR(S) : Marsha A. Moses et al.

Page 1 of 1

It is certified that error appears in the above-identified patent and that said Letters Patent is hereby corrected as shown below:

In the Claims

In Claim 1, at Column 24, Line 65:
"(CAMP)"

Should read:
--(cAMP)--.

Signed and Sealed this
Sixth Day of May, 2025

Coke Morgan Stewart
*Acting Director of the United States Patent and Trademark Office*